United States Patent
Puri et al.

(10) Patent No.: US 12,427,123 B2
(45) Date of Patent: Sep. 30, 2025

(54) PHENYLEPHRINE HYDROCHLORIDE COMPOSITIONS AND CONTAINERS

(71) Applicant: Endo Operations Limited, Dublin (IE)

(72) Inventors: Reema Ajitkumar Puri, Hillsborough, NJ (US); Harshil H. Jain, Monmouth Junction, NJ (US); Tushar Hingorani, Bridgewater, NJ (US); Kumaresh Soppimath, Skillman, NJ (US)

(73) Assignee: Endo Operations Limited, Dublin (IE)

( * ) Notice: Subject to any disclaimer, the term of this patent is extended or adjusted under 35 U.S.C. 154(b) by 0 days.

(21) Appl. No.: 18/751,134

(22) Filed: Jun. 21, 2024

(65) Prior Publication Data

US 2024/0366532 A1 Nov. 7, 2024

Related U.S. Application Data

(63) Continuation of application No. 17/154,516, filed on Jan. 21, 2021.

(60) Provisional application No. 62/964,457, filed on Jan. 22, 2020.

(51) Int. Cl.
| | | |
|---|---|---|
| *A61K 31/137* | (2006.01) | |
| *A61K 9/00* | (2006.01) | |
| *A61K 47/02* | (2006.01) | |
| *A61K 47/12* | (2006.01) | |
| *A61K 47/18* | (2017.01) | |
| *B65B 3/00* | (2006.01) | |
| *B65D 75/38* | (2006.01) | |
| *B65D 81/26* | (2006.01) | |

(52) U.S. Cl.
CPC .......... *A61K 31/137* (2013.01); *A61K 9/0019* (2013.01); *A61K 47/02* (2013.01); *A61K 47/12* (2013.01); *A61K 47/183* (2013.01); *B65B 3/003* (2013.01); *B65D 75/38* (2013.01); *B65D 81/266* (2013.01)

(58) Field of Classification Search
CPC ... A61K 31/137; A61K 47/183; A61K 9/0019
See application file for complete search history.

(56) References Cited

U.S. PATENT DOCUMENTS

| | | | | |
|---|---|---|---|---|
| 5,896,989 A | * | 4/1999 | Ropiak | A61J 1/16 604/408 |
| 2007/0249566 A1 | * | 10/2007 | Martin | A61K 31/519 514/217 |
| 2021/0386858 A1 | * | 12/2021 | Bastos Silva | A61K 47/34 |
| 2022/0023201 A1 | * | 1/2022 | McAnany | A61K 9/0019 |

* cited by examiner

*Primary Examiner* — Andrew S Rosenthal
(74) *Attorney, Agent, or Firm* — ArentFox Schiff & Endo

(57) ABSTRACT

A ready-to-administer antioxidant free phenylephrine compositions has improved stability and is optionally free of metal chelating agents. Contemplated compositions are preferably packaged into a flexible polymer bag and maintain degradation of the phenylephrine at remarkably low levels, even over extended storage periods.

19 Claims, 4 Drawing Sheets

PHENYLEPHRINE HYDROCHLORIDE COMPOSITIONS AND CONTAINERS

This application is a continuation of U.S. patent application Ser. No. 17/154,516, filed on Jan. 21, 2021, which claims priority to U.S. US Provisional Patent Application No. 62/964,457, filed on Jan. 22, 2020, the disclosures of which are incorporated by reference herein.

FIELD OF THE INVENTION

The field of the invention pharmaceutical compositions and methods, and particularly as they relate to stable, sterile and ready-to-administer antioxidant free phenylephrine compositions, uses, and methods of manufacturing and packaging same.

BACKGROUND OF THE INVENTION

The background description includes information that may be useful in understanding the present disclosure. It is not an admission that any of the information provided herein is prior art or relevant to the presently claimed invention, or that any publication specifically or implicitly referenced is prior art.

All publications and patent applications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Phenylephrine hydrochloride as shown below is an α-adrenergic receptor agonist, used primarily as a decongestant, as an agent to dilate the pupil, and to increase blood pressure in adults with clinically important hypotension resulting primarily from vasodilation, in such settings as septic shock or anesthesia.

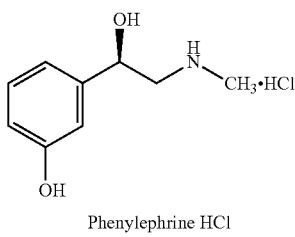

Phenylephrine HCl

Interaction of phenylephrine with $\alpha_1$-adrenergic receptors on vascular smooth muscle cells causes activation of the cells and results in vasoconstriction. Following intravenous administration of phenylephrine hydrochloride, increases in systolic and diastolic blood pressures, mean arterial blood pressure, and total peripheral vascular resistance are observed. The onset of blood pressure increase following an intravenous bolus of phenylephrine hydrochloride is rapid, typically within minutes. As blood pressure increases following intravenous administration, vagal activity also increases, resulting in reflex bradycardia. Phenylephrine has activity on most vascular beds, including renal, pulmonary, and splanchnic arteries.

Phenylephrine is available as an over-the-counter nasal decongestant, either alone or in combination with other cold remedies. Intravenous phenylephrine has been available and marketed for several decades. In ophthalmology, ophthalmic preparations (e.g., eye drops) of phenylephrine or phenylephrine combinations have been used to induce mydriasis, as a provocative test for angle-closure glaucoma, and as an adjunct in the treatment of anterior uveitis and secondary glaucoma.

Pharmacokinetics for phenylephrine following intravenous administration follows a 2-compartment model with rapid distribution (α-phase half-life<5 min) from the central compartment to peripheral tissues and end organs. Phenylephrine is extensively metabolized by the liver (primarily by monoamine oxidase and sulfotransferase), with only 12% of the dose excreted unchanged in the urine. The primary metabolic pathway is deamination by monoamine oxidase, forming the major metabolite, 3-hydroxymandelic acid. Following i.v. administration, phenylephrine and its metabolites are primarily eliminated in the urine. These metabolites are inactive with respect to $\alpha_1$- and $\alpha_2$-adrenergic receptors.

Phenylephrine hydrochloride is very soluble in water, freely soluble in ethanol, and insoluble in chloroform and ethyl ether. Phenylephrine hydrochloride is sensitive to light. Phenylephrine has been reported to be stable below pH 7.3, above pH 7, the degradation occurs on the side chain with loss of secondary amine function, and the phenolic group remains stable.

Currently, phenylephrine hydrochloride for intravenous use is marketed as Phenylephrine hydrochloride solution, 10 mg/mL, USP solution concentrate by West Ward Pharmaceuticals. It is available as a concentrate (10 mg/mL) as a single-dose 1 mL vial (10 mg of phenylephrine hydrochloride per vial), Phenylephrine hydrochloride solution is a clear colorless, sterile, non-pyrogenic solution for intravenous use and must be diluted before administration as an intravenous bolus or continuous intravenous infusion. Each mL contains phenylephrine hydrochloride 10 mg, sodium chloride 3.5 mg, sodium citrate dihydrate 4 mg, citric acid monohydrate 1 mg, and sodium metabisulfite 2 mg in water for injection. The pH is adjusted with sodium hydroxide/or hydrochloric acid if necessary, to a pH range of 3.0 to 6.5.

The concentrate must be diluted prior to use and requires personnel intervention, there is a possibility of microbial contamination or dilution error. Even more significantly, the diluted solution should not be held for more than 4 hours at room temperature or for more than 24 hours under refrigerated condition.

Thus, even though various phenylephrine hydrochloride formulations are known in the art, extended stability at low and ready-to-use concentrations is problematic. In addition, presence of metabisulfite in known compositions may lead to undesirable side effects in at least some subjects. Consequently, there is a need for improved stable, low concentration, ready-to-administer antioxidant free phenylephrine hydrochloride formulations, and methods of manufacturing and storing the same.

SUMMARY OF THE INVENTION

The present inventive subject matter is directed to various phenylephrine formulations in an aqueous solution that are antioxidant free and that enhance or preserve the chemical stability of phenylephrine at low (especially at ready-to-use) concentrations and consequently extend the product shelf life of such ready-to-use products with little to no degradation products formed from phenylephrine after storage at ambient temperatures over extended periods (e.g., at least 6 months). Advantageously, contemplated compositions are sterile, and in some cases will also not include a metal ion chelator.

In one aspect of the inventive subject matter, the inventors contemplate a ready-to-administer sterile antioxidant free phenylephrine composition that includes phenylephrine at a concentration of equal or less than 0.4 mg/ml, an optional metal ion chelator, and an acetate buffer, wherein the composition has a pH of between 4.5 and 5.5. Advantageously no more than 0.5% degradation products are formed from degradation of the phenylephrine upon storage of the phenylephrine composition over a period of at least six months at 25° C.

In some embodiments, the phenylephrine is present in the composition at a concentration of about 0.04 mg/ml, or at a concentration of about 0.08 mg/ml, or at a concentration of about 0.16 mg/ml, or at a concentration of about 0.4 mg/ml or at a concentration of 0.8 mg/mL. Typically, but not necessarily, the acetate buffer has a concentration of equal or less than 5 mM, and/or the composition has a pH of about 5.0.

In further embodiments, contemplated compositions comprise a tonicity agent (e.g., sodium chloride, glycerol, thioglycerol, mannitol, lactose, or dextrose), and/or include the metal ion chelator. Suitable metal ion chelators especially include ethylene diamine tetra acetic acid (EDTA), and it is generally preferred that metal ion chelator is present in an amount of equal or less than 10 µg/mL.

Where desired, the composition may be packaged in a flexible polymer bag, which may in turn be further packaged into a metallized pouch that may or may not include an oxygen scavenger.

For example, contemplated ready-to-administer sterile antioxidant free phenylephrine composition may essentially consist of phenylephrine at a concentration of between about 0.04 mg/ml and about 0.4 mg/ml, an acetate buffer, wherein the composition has a pH of between 4.5 and 5.5 (e.g., about 5.0), and an optional metal ion chelator and an isotonicity adjusting agent. As noted, before, no more than 0.15% degradation products are typically formed from degradation of the phenylephrine upon storage of the phenylephrine composition over a period of at least six months at 25° C.

In further examples, phenylephrine is present at a concentration of about 0.04 mg/ml, or about 0.08 mg/ml, or about 0.16 mg/ml, or about 0.4 mg/ml. Where a metal ion chelator is included, it is generally preferred that the metal ion chelator is present in an amount of equal or less than 10 µg/mL.

In another aspect of the inventive subject matter, the inventors also contemplate a method of manufacturing a ready-to-administer sterile antioxidant free phenylephrine composition that will include a step of formulating a buffered liquid including phenylephrine or salts thereof. Most typically, the buffered composition comprises an acetate buffer and has a pH of between 4.5 and 5.5, and optionally further comprises a metal ion chelator, and it is preferred that in such methods the phenylephrine is present in the buffered liquid at a concentration of equal or less than 0.4 mg/ml. As will be appreciated, contemplated methods further include a step of terminally sterilizing the liquid composition. Advantageously no more than 0.15% degradation products are formed from degradation of the phenylephrine upon storage of the so prepared phenylephrine composition over a period of at least six months at 25° C.

Suitable phenylephrine concentrations in such methods include about 0.04 mg/ml, about 0.08 mg/ml, about 0.16 mg/ml, and about 0.4 mg/ml. It is further preferred that the acetate buffer has a concentration of equal or less than 5 mM, and/or that the composition has a pH of about 5.0. Where the composition comprises the metal ion chelator, it is generally preferred that the metal ion chelator is ethylene diamine tetra acetic acid (EDTA), and/or that the metal ion chelator is present in an amount of equal or less than 10 µg/mL. In further aspects of contemplated compositions, the composition further comprises a tonicity agent such as sodium chloride, glycerol, thioglycerol, mannitol, lactose, and dextrose.

Most typically, terminal sterilization will include a step of filling the liquid solution in a primary bag (such as a flexible polymer bag with a stopper), followed by placing the filled primary bag in a metallized pouch that optionally contains an oxygen scavenger and are sealed. Methods presented herein may include autoclaving the liquid contained in the sealed secondary bag (which may optionally contain an oxygen scavenger).

In yet another aspect of the inventive subject matter, the inventors also contemplate a method of increasing blood pressure in an individual that includes a step of administering the ready-to-inject phenylephrine composition presented herein. For example, the ready-to-inject phenylephrine composition may be administered as a bolus to thereby deliver between 40-100 µg phenylephrine, and/or may be administered as a continuous intravenous infusion to thereby deliver between 10 and 40 µg/min phenylephrine. Most typically, the ready-to-inject phenylephrine composition is administered without further dilution.

Various objects, features, aspects, and advantages will become more apparent from the following detailed description of preferred embodiments, along with the accompanying drawing in which like numerals represent like components.

DETAILED DESCRIPTION

Figure 1:
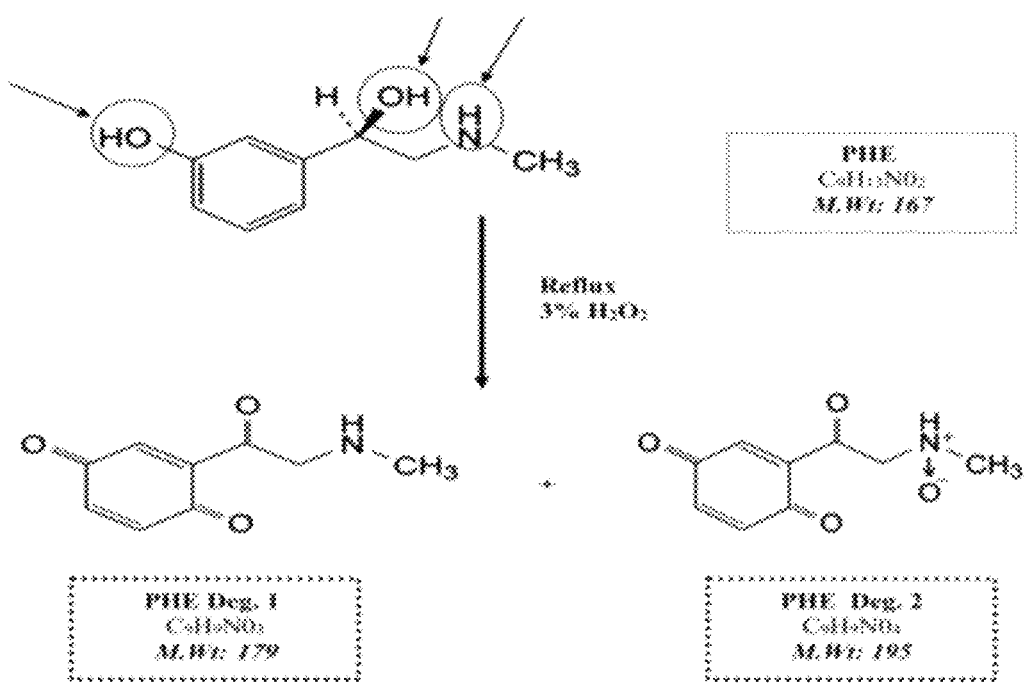
FIG. 1 is an exemplary illustration of oxidative degradation of phenylephrine.

The inventors have now discovered that stable aqueous and ready-to-use aqueous pharmaceutical formulations of phenylephrine or its pharmaceutically acceptable salts can be prepared in a conceptually simple and effective manner. Advantageously, such formulations are antioxidant free, may or may not include a metal ion chelator, have a phenylephrine concentration of between 40-400 mcg/mL, and more preferably between 10-100 mcg/mL, and have a physiologically desirable pH of between 4.5 and 5.5. As used herein, the term "phenylephrine" should be interpreted broadly to include pharmaceutically acceptable salts and prodrugs thereof.

Unexpectedly, and in spite of the known instability of low-concentration phenylephrine formulations, the inventors discovered that phenylephrine compositions could be prepared that contain phenylephrine or salts thereof at a concentration suitable for direct administration (i.e., without the need for dilution prior to administration) and that could be stored over months without significant degradation. Moreover, the inventors also surprisingly found that storage stability of phenylephrine was significantly affected by the choice of buffering agent, especially at low concentrations of phenylephrine as is shown in more detail below. In particular, where acetate was used as a buffering agent, stability of low concentration phenylephrine was significantly increased as compared to a citrate or tartrate buffer with everything else being equal. Moreover, contemplated compositions were also thermally stable and thus allowed for terminal sterilization.

In one aspect of the inventive subject matter, the inventive subject matter is directed to a stable aqueous pharmaceutical preparation of phenylephrine or its pharmaceutically acceptable salts in a ready-to-use form where the pharmaceutical preparation is sterile and packaged in a polymeric (preferably flexible) bag for infusion or in a blow-fill-seal (BFS) container. Particularly preferred formulations are ready-to-administer, anti-oxidant free phenylephrine infusion formulations that include phenylephrine hydrochloride at low concentrations, such as about 0.04 mg/ml, or about 0.08 mg/ml, or about 0.16 mg/ml, or about 0.4 mg/ml, and have a pH of between 3.0-6.0, preferably between 4.5-6.0, and more preferably between 4.5-5.5 (e.g., about 5.0). As is also shown in more detail below, such formulations may contain a metal ion chelating agent or may be chelating agent free and an isotonicity adjusting agent such as dextrose or sodium chloride, more preferably sodium chloride.

In this context, it should be recognized that while phenylephrine is stable as a solid, it will readily degrade in an aqueous solution following various complex and distinct degradation mechanisms, which at least in part will depend on the particular pH. The inventors generated predicted ionization constants using known algorithms (Chemicalize, commercially available program from ChemAxon) and exemplary results are shown immediately below. Here, the strongest acidic pKa (pKa: 9.07) is seen on the phenolic hydroxyl group, while the strongest basic pKa (pKa: 9.69) is on the amine functionality.

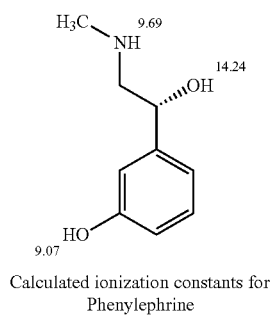

Calculated ionization constants for Phenylephrine

As will be readily appreciated, the different ionization stages of phenylephrine are dependent on the pH of the solution in which phenylephrine is present. Thus, phenylephrine can be present in aqueous solutions in neutral (unionized) form, in cationic form, anionic form (single or double negative charge), or in zwitterionic form. As should also be appreciated, the ionization state of phenylephrine will influence the rate and type of degradation. Among other degradation mechanisms, phenylephrine can undergo degradation via oxidation. pH dependent cyclization, aldehyde dependent phenolic cyclization, and furan dependent cyclization. Notably, phenylephrine is not subject to racemization as a function of pH, and phenylephrine is optically stable in solutions at pH 3.0 and pH 6.0.

Figure 2:
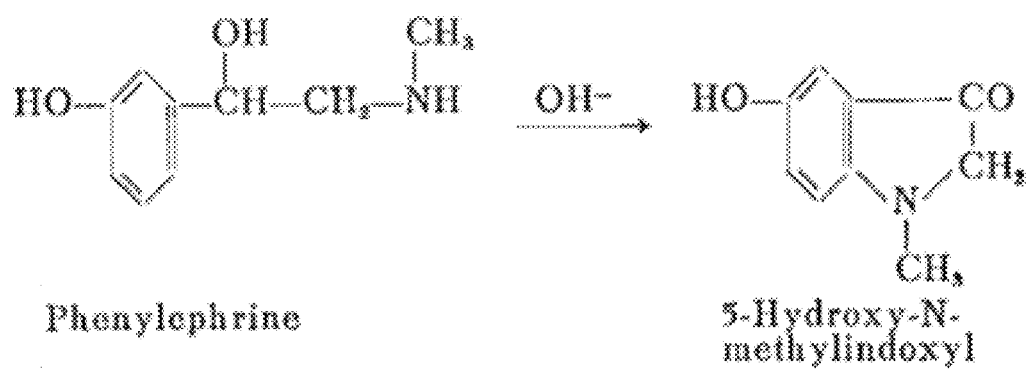
FIG. 2 is an exemplary illustration of pH dependent cyclization of phenylephrine.

Oxidative degradation of phenylephrine occurs through the oxidation of the phenolic and secondary alcohol moieties, with the liberation of four hydrogens. This mechanism then produces the corresponding quinone, and the degradation of ketone (PHE Deg. 1, with an MW of 179 Da), and further oxidation of the secondary amine to the corresponding nitrone takes place to yield the second degradation (PHE Deg. 2, with an MW of 195 Da) as shown in FIG. 1. A pH dependent cyclization of phenylephrine has been shown to proceed via a pH dependent pathway. Around pH 7, degradation of phenylephrine involves the side chain with loss of the secondary amine function under retention of the phenolic group. The decomposition products have not been identified but 5-hydroxy-N-methyl indoxyl has been proposed as is shown in FIG. 2.

Figure 3:
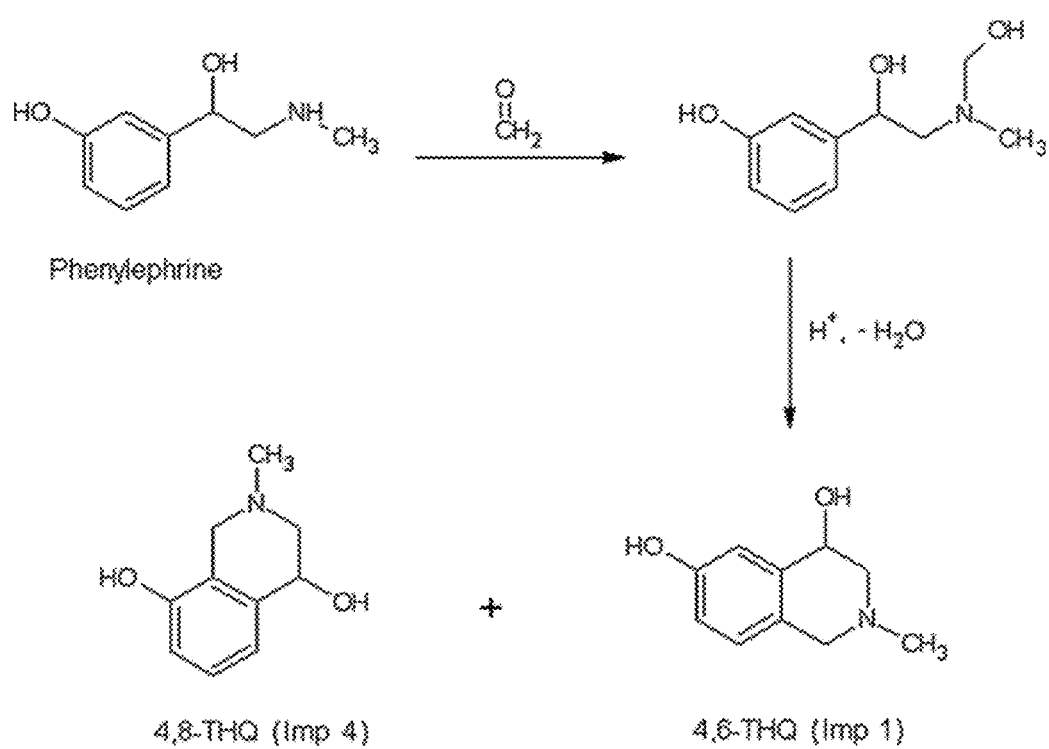
FIG. 3 is an exemplary illustration of aldehyde dependent phenolic cyclization of phenylephrine.
Figure 4:
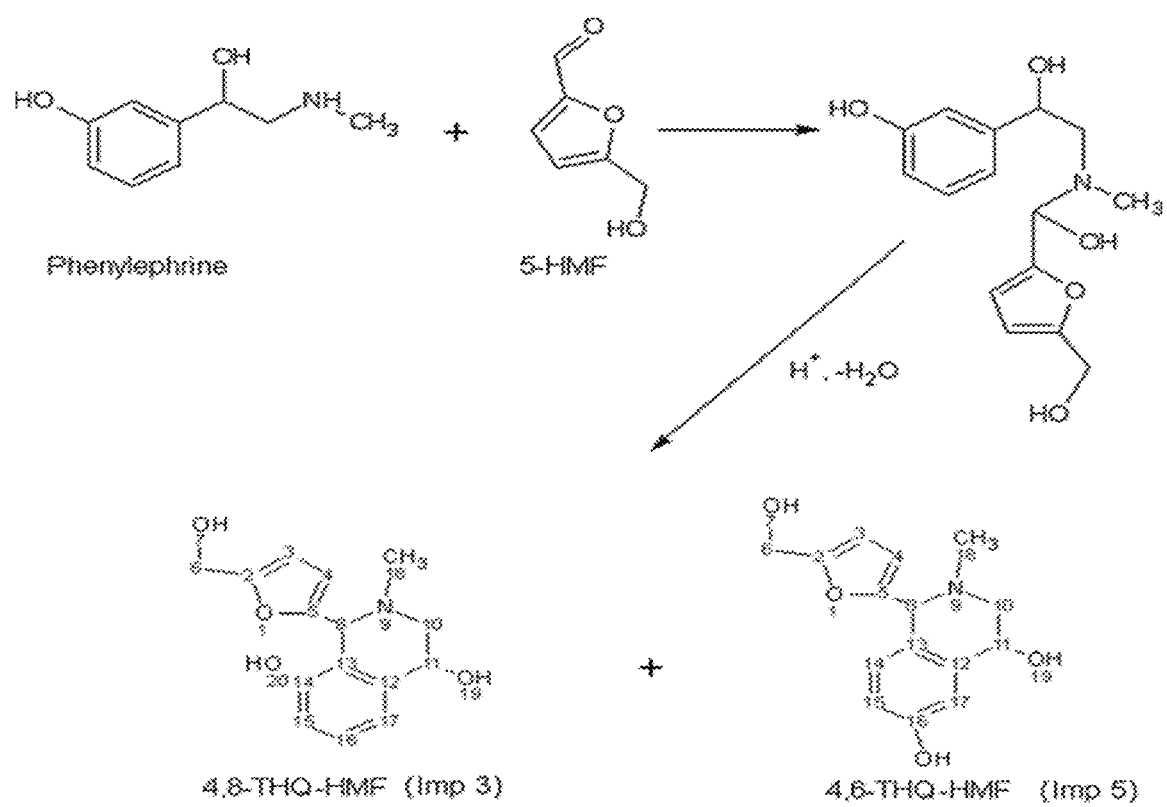
FIG. 4 is an exemplary illustration of furan dependent phenolic cyclization of phenylephrine

Phenylephrine also degrades in the presence of formaldehyde as shown in FIG. 3 in an aldehyde dependent phenolic cyclization. Here, cyclization is a very fast reaction within a wide pH range. This reaction sequence is also known as a "phenolic cyclization" and typically leads to formation of tetrahydroisoquinolines (THQs). In FIG. 3 the degradation product Imp 1 corresponds to 4,6-dihydroxy N-methyl-1,2,3,4-tetrahydroisoquinoline, and the degradation product Imp 4 corresponded to 4,8-dihydroxy-N-methyl-1,2,3,4-tetrahydroisoquinoline. FIG. 4 depicts yet another degradation mechanism of phenylephrine, a furan dependent cyclization. Here, formation of Imp 3 and Imp 5 are attributable to reaction of phenylephrine with a furan. It is known that the primary sources of thermally produced furan and its derivatives (such as 5-HMF) are saccharides. The highest potential to produce 5-HMF upon thermal treatment has glucose, originating from saccharose hydrolysis, for example, during autoclaving. Similarly, in another reaction sequence (phenolic cyclization), there is the possibility of condensation of 5-HMF with phenylephrine, thereby forming 1-[5-(hydroxymethyl)-2-furyl]-2-methyl-1, 2,3,4-tetrahydroisochinolin-4,8-diol (4,8-THQ-HMF) and 1-[5-(hydroxymethyl)-2-furyl]-2-methyl-1,2,3,4-tetrahydroisochinolin-4,6-diol (4,6-THQ-HMF) as also shown in FIG. 4.

Despite the various degradation routes, and as is described in more detail below, contemplated aqueous pharmaceutical preparation of phenylephrine hydrochloride in a ready-to-use form were remarkably stable at room temperature (e.g., 25° C. 60% relative humidity). Degradation products from the degradation of phenylephrine in solution remained within acceptable limits (e.g., less than 10 wt %, less than 5 wt %, less than 2 wt %, less than 1 wt %, less than 0.7 wt %, less than 0.6 wt %, less than 0.5 wt %, less than 0.4 wt %, less than 0.3 wt %, less than 0.2 wt %, less than 0.1 wt %) over long term storage (e.g., at least 1 month, at least 2 months, at least 3 months, at least 6 months, at least 9 months, at least 12 months, at least 18 months). Therefore, the phenylephrine formulations of the inventive subject matter can be provided in a ready-to-use form to avoid the inconvenience and time associated with diluting a concentrated small volume phenylephrine parenteral formulation into infusion diluents prior to infusion. Thus, the ready-to-use formulations also eliminate microbial contamination risks and calculation errors associated with dilution.

For example, exemplary contemplated formulations may contain phenylephrine hydrochloride as the active ingredient at a concentration of 40 mcg/mL, 80 mcg/mL, 160 mcg/mL, or 400 mcg/mL as indicated in Table 1 below. These solutions may contain glacial acetic acid as a buffering agent, optionally ethylene diamine tetra acetic acid (EDTA) as a metal chelator, sodium chloride for isotonicity and water for injection as a vehicle. Hydrochloric acid/sodium hydroxide are used as pH adjusting agents, and the resulting solutions are then filled in a 250 mL non-PVC IV bag and terminally sterilized. Following sterilization, the IV bag can be placed in an aluminum overwrap which may or may not include an oxygen scavenger. Alternatively, the resulting solution can be filled in a 250 mL non-PVC IV bag and then placed in a secondary packaging (such as metallized pouch with or without oxygen scavenger, optionally flushed with an inert gas such as nitrogen) and then terminally sterilized.

TABLE 1

| Ingredient | Quantity (mg/mL) | | | |
|---|---|---|---|---|
| Phenylephrine Hydrochloride | 0.04 | 0.08 | 0.16 | 0.4 |
| Sodium chloride | 8.46 | 8.46 | 8.46 | 8.46 |
| Glacial Acetic Acid | 0.3 | 0.3 | 0.3 | 0.3 |
| EDTA (Titriplex III) | 0.01 | 0.01 | 0.01 | 0.01 |
| Hydrochloric acid/ sodium hydroxide | q.s. to pH 5.0 | q.s. to pH 5.0 | q.s. to pH 5.0 | q.s. to pH 5.0 |
| Water | q.s. to 1.0 mL | q.s. to 1.0 mL | q.s. to 1.0 mL | q.s. to 1.0 mL |

However, it should be appreciated that contemplated formulations can be prepared in a range of concentrations commonly required by medical practitioners for emergency restoration of blood pressure in cases of anesthesia, among other suitable uses. For example, phenylephrine can be present in contemplated formulations at a concentration of between 0.001 to 0.2% w/v, or between 0.001 to 0.01% w/v, or between 0.004 to 0.04% w/v, etc. Therefore, contemplated phenylephrine concentrations are 10-50 mcg/mL, 30-70 mcg/mL, 50-100 mcg/mL, 75-150 mcg/mL. 100-200 mcg/mL, 300-500 mcg/mL. 400-700 mcg/mL, 500-1,000 mcg/mL, and even higher. Of course, it should also be appreciated that phenylephrine may be present as a non-salt or in a salt form, and all pharmaceutically acceptable salts are deemed suitable for use herein. Therefore, suitable salt forms include phenylephrine hydrochloride, phenylephrine hydrobromide, etc.

Some contemplated formulations will include phenylephrine hydrochloride and a vehicle without preservatives, and particularly without anti-oxidants and/or metal ion chelating agents, while in other aspects contemplated formulations will include at least one excipient. Regardless of the particular form of preparation, contemplated formulations may further include stabilizing agents, buffer components, and isotonicity adjusting agents.

For example, tonicity agents, such as sodium chloride, glycerol, thioglycerol, mannitol, lactose, dextrose and the like can be included in some contemplated compositions. The amount of tonicity adjusting agent used can be adjusted to obtain osmolality of the formulations in the range of 260 to 340 mOsm/kg. An osmometer can be used to check and adjust the amount of tonicity adjusting agent to be added to obtain the desired osmolality. Additionally, or alternatively, contemplated formulations may include further pharmaceutically acceptable excipients, and especially buffers, and any reasonable mixture thereof. Among other choices, contemplated buffers include buffer systems in which an organic or inorganic acid and a corresponding salt form the buffer system as well as amphoteric compounds (e.g., HEPES, MES, etc.). Most typically, the buffer will be a pharmaceutically acceptable buffer that is present at a relatively low concentration.

For example, suitable buffers include acetate buffers, citrate buffers, and tartrate buffers. However, and as is described in more detail below, the inventors surprisingly discovered that particularly at relatively low concentrations (e.g., equal or less than 400 mcg/mL, equal or less than 200 mcg/mL, equal or less than 100 mcg/mL, equal or less than 70) mcg/mL, equal or less than 40 mcg/mL, equal or less than 20 mcg/mL, equal or less than 10 mcg/mL) of phenylephrine, not all buffers provided equal stability to the phenylephrine. Indeed, at increasingly lower concentrations (e.g., equal or less than 100 mcg/mL, equal or less than 70 mcg/mL, equal or less than 40 mcg/mL, equal or less than 20 mcg/mL, equal or less than 10 mcg/mL) of phenylephrine, the choice of buffer had an increasingly significant impact on stability of phenylephrine, especially at a lower concentration.

This effect was pronounced at relatively low concentrations of the buffering agents, and typical low concentrations include equal or less than 20 mM, equal or less than 10 mM, equal or less than 5 mM, equal or less than 3 mM, or equal or less than 20 mM as is demonstrated in more detail below. Therefore, in especially preferred aspects of the inventive subject matter, the buffer is acetate buffer at a strength of equal or less than 5 mM, or equal or less than 5 mM, particularly where the phenylephrine concentration is equal or less than 100 mcg/mL, equal or less than 70 mcg/mL, equal or less than 40 mcg/mL, equal or less than 20 mcg/mL, equal or less than 10 mcg/mL.

In this context, it should be appreciated that contemplated compositions are ready-to-administer formulations and that the administered volume will typically be relatively large (e.g., at least 10 mL or at least 50 mL, or at least 100 mL, or at least 200 mL, or at least 300 mL, or at least 400 mL, or at least 500 mL). Consequently, the buffer strength must be relatively low so as to avoid adverse effects of adding substantial quantities of buffer to the circulation of an individual. Notably, the inventors discovered that a desirable pH range can be achieved at a low buffer concentration that afforded phenylephrine stability over extended storage.

It should further be appreciated that depending on the particular ingredients, the pH of the formulation may vary. However, it is generally preferred that the pH of the formulations is suitable for injection and will typically be between 3.0 and 7.0, more typically between 4.7 and 6.0. For example, contemplated pH ranges will be between 4.5-5.0, or between 4.7-5.2, or between 4.9-5.4, or between 5.1-5.6, or between 5.3-5.8, or between 5.5-6.0, or between 5.7-6.2, or between 5.9-6.4, or between 6.1-6.4, or between 6.3-6.6, or between 6.5-6.8, or between 6.7-7.0. Thus, suitable pH may be 4.0, or 4.1, or 4.2, or 4.3, or 4.4, or 4.5, or 4.6, or 4.7, or 4.8, or 4.9, or 5.0, or 5.1, or 5.2, or 5.3, or 5.4, or 5.5, or 5.6, or 5.7, or 5.8, or 5.9, or 6.0 (each +/−0.2 pH units). As will be readily appreciated, the pH can be maintained using any suitable buffer system, and all buffer systems with buffer capacity in the above noted pH values/ranges are deemed appropriate for use herein.

In at least some embodiments, contemplated formulations may also include one or more chelating agents, and particularly metal ion chelators. For example, suitable chelators include various bicarboxylic acids, tricarboxylic acids, and aminopolycarboxylic acids such as ethylenediaminetetraacetic acid (EDTA), ethylene glycol-bis(β-aminoethyl ether)-N,N,N',N'-tetraacetic acid (EGTA), and penta(carboxymethyl)diethylenetriamine (DTPA), and salts and hydrates thereof. While not limiting to the inventive subject matter, it is contemplated that the metal ion chelators will slow down both the baseline and metal ion-stimulated oxidation of phenylephrine. Remarkably, the inventors unexpectedly observed that the desirable effect of the chelators was observable at relatively low concentrations of the chelators. For example, reduction of the baseline and metal ion-stimulated autoxidation of Phenylephrine was observed at chelator concentrations of between 1 μg/ml and 10 μg/ml as is shown in more detail below. Therefore, metal ion chelators can be included at concentrations of between 1 μg/ml and 10 μg/ml, or between 5 μg/ml and 20 μg/ml, or between 20 μg/ml and 50 μg/ml, or between 50 μg/ml and 100 μg/ml. The term "metal ion chelator" as used herein refers to multi-dentate compounds that complex metal cations and that have no other significant physiological role (e.g., metabolite) in a mammal. Therefore. EDTA is deemed a metal ion chelator whereas citrate or tartrate are not deemed a metal chelator.

For the purpose of improving the stability of aqueous formulation of phenylephrine or hydrochloride salt thereof, which are susceptible to oxidation, the action of the oxygen can be reduced or even prevented by eliminating or neutralizing oxygen. Optional inert gas sparging (by bubbling/purging the solution with nitrogen and/or any other inert gas such as argon, helium, freons, xenon) can be carried out during any of the manufacturing steps. In one example, an aqueous solution was purged with an inert gas under the reduced pressure. The injectable solutions of the inventive subject matter may have a particularly low content of oxygen dissolved in the solvent water, typically less than 4 ppm less, or than 2 ppm, or more preferably less than 1 ppm. A chelating agent can be dissolved in the solution for injection, followed by addition of sodium chloride. As will be readily appreciated, further modifications in the generalized process can be made as known to the person skilled in the art.

In yet further contemplated aspects, it should be appreciated that desirable stability can be achieved with contemplated compositions in the absence of a chelator and/or an antioxidant. Such is particularly beneficial where chelators would have an otherwise undesirable effect and/or where side effects for antioxidants should be reduced or avoided. Thus, and viewed from a different perspective, contemplated compositions can be prepared without addition of EDTA and/or sulfites.

With respect to sterilization it is noted that the bulk solutions can be filtered through a 0.22 micron filter, and filled into a polyethylene, polypropylene or low-density polyethylene containers in a blow-fill-seal process. BFS is a form of advanced aseptic manufacturing wherein the container is formed, filled, and sealed in one continuous, automated system not requiring human intervention. The process begins with the extrusion of plastic granules in the form of a hot hollow pipe of molten plastic called a parison. The next step is the blow molding of the container with an open top through which the container is filled-all while the plastic remains hot and in a molten state. Once filled, the container is hermetically sealed and cooled. The blow-fill seal process can take several seconds, and contemplated ready-to-administer compositions advantageously are formulated to withstand the temperature and pressure requirements without substantial degradation of phenylephrine (e.g., less than 10 wt %, less than 5 wt %, less than 2 wt %, less than 1 wt %, less than 0.7 wt %, less than 0.6 wt %, less than 0.5 wt %, less than 0.4 wt %, less than 0.3 wt %, less than 0.2 wt %, less than 0.1 wt % degradation) over long term storage (e.g., at least 1 month, at least 2 months, at least 3 months, at least 6 months, at least 9 months, at least 12 months, at least 18 months). Under the conditions tested, the assays indicated that if water for injections contained between 0.1 to 8.4 ppm of dissolved oxygen preferably less than 5 ppm, preferably less than 2 ppm, preferably less than 1 ppm, and the residual oxygen content into the primary packaging was between 0.01 to 20%, preferably less than 10%, preferably less than 5%, preferably less than 1%, such conditions assisted in improving the stability of phenylephrine hydrochloride. Thus, reduction of dissolved oxygen with inert gas as described above is deemed suitable for such processes as well.

Once the phenylephrine formulations are filled in large volume polymeric, semi-permeable infusion containers manufactured via BFS technology and or flexible IV bags, the containers can optionally be layered or covered with a secondary packaging system including an aluminum pouch and/or other oxygen scavenger. For example, the BFS containers can further be sealed in an oxygen and moisture barrier blister packaging. The blister packaging can comprise one or more layers, and the one or more layers can include aluminum foil or other oxygen absorber having an oxygen transmission rate (OTR) between 0.0005 to 5.00 cc/100 in$^2$/24 hrs. Additionally or alternatively, one or more oxygen absorbers (metal or metal free, organic material) can be incorporated into any portion of the BFS container, the secondary packaging system, or between the two (e.g., between the BFS container and the multi-layer packaging) such that the oxygen absorber removes at least a portion of oxygen from the air surrounding said oxygen-sensitive drug.

It should further be appreciated that contemplated formulations will be sterilized, and all known manners of sterilization are deemed suitable for use herein, including filtration through a 0.22 micron filter, heat sterilization, radiation (e.g., gamma, electron beam, microwave), and/or ethylene oxide sterilization to render the formulations sterile.

The optimum therapeutically effective amount of a drug is the amount of the drug in the composition that will yield the most effective results in terms of efficacy of treatment in a given subject. This amount can vary depending upon a variety of factors, including but not limited to the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, for instance, by monitoring a subject's response to administration of a compound and adjusting the dosage accordingly. For additional guidance, see Remington: The Science and Practice of Pharmacy (Gennaro ed. 20th edition, Williams & Wilkins PA, USA) (2000). Moreover, and depending on the particular purpose, it should also be recognized that contemplated compositions may be combined (in vivo, or in a therapeutic formulation or administration regimen) with at least one other therapeutically active agent to additively or synergistically provide a therapeutic or prophylactic effect.

Figure 5:
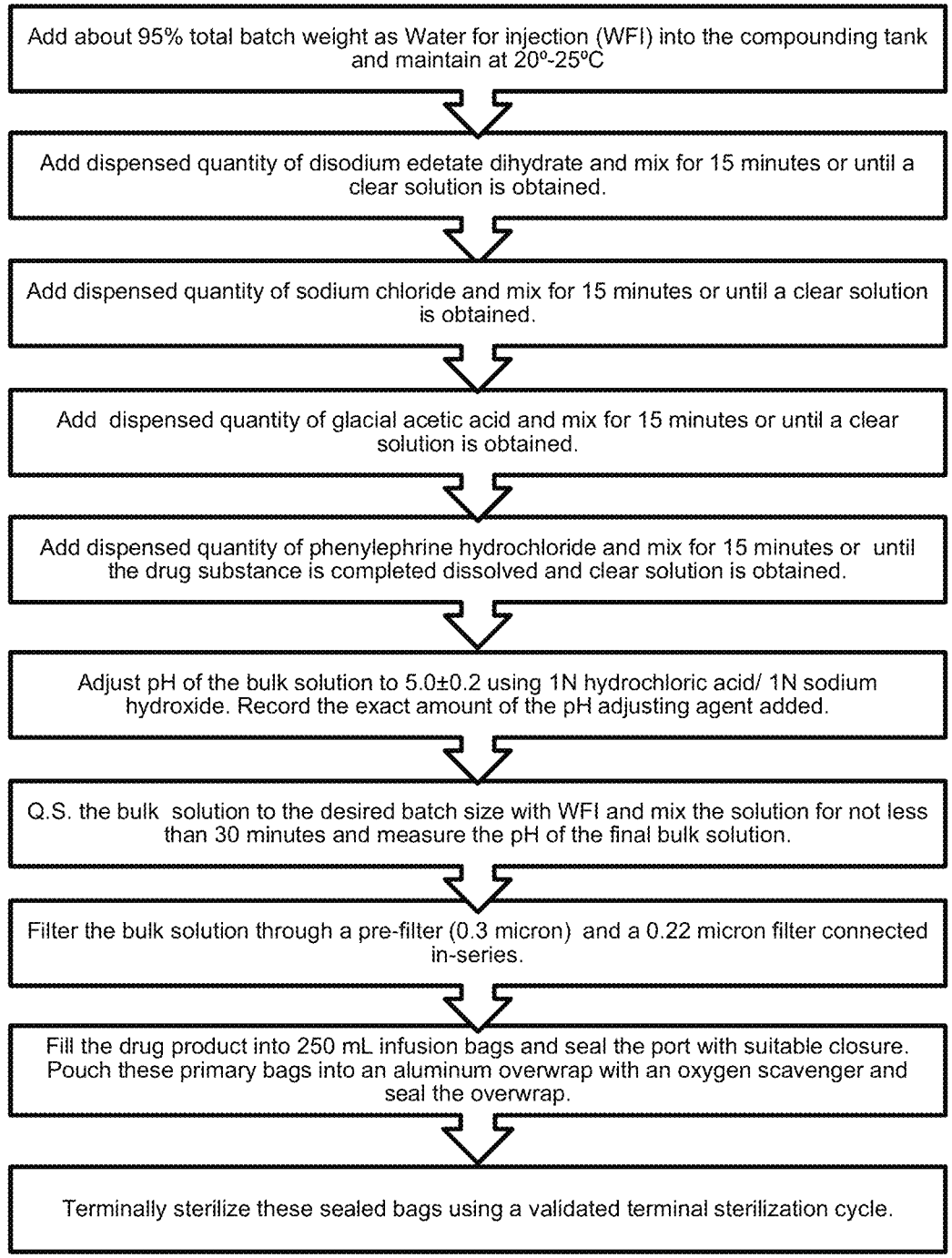
FIG. 5 is an exemplary flow chart depicting a manufacturing process for phenylephrine compositions contemplated herein.

In further contemplated aspects, it should be appreciated that the phenylephrine formulations presented herein can be prepared in a variety of methods, and all manners of production are deemed suitable for use herein. For example, in one embodiment as also schematically depicted in FIG. 5, water for injection is used as the carrier and is admixed with a desired quantity of EDTA until completely dissolved, to which then sodium chloride as tonicity agent is added. Once the sodium chloride is completely dissolved, acetic acid is added in a desired amount and allowed to completely dissolve after which phenylephrine hydrochloride is compounded into the so prepared solution. The pH is then adjusted to pH 5.0 +/−0.2 using pH adjusting agents such as hydrochloric acid or sodium hydroxide and the so prepared solution is brought to the desired final volume using water for injection. Upon final pH correction, the solution is filtered through a 0.22 micron filter and filled into suitable containers such as polymeric (e.g., polypropylene) flexible bags at a desired volume (e.g., 250 mL). The bags are then sealed and placed into a metallized overwrap as secondary container. Preferably, an oxygen scavenger is included into the space between the metallized overwrap and the inner container, the space is optionally flushed with an inert gas, and once the overwrap is sealed, the sealed bags are subjected to terminal sterilization using an autoclaving process. Sterilization can also be performed using processes other than autoclaving such as gamma irradiation e-beam sterilization, etc. However, autoclaving is typically preferred.

Examples

The following examples are provided for illustrative purposes only and should not be interpreted as limiting the present invention. Unless noted otherwise, all quantities indicated in % are weight percent following the general analytical protocol as indicated below.

Analytical protocol: phenylephrine hydrochloride (PEP) assay is performed using an isocratic reversed-phase HPLC-UV method. Biphenyl-modified core-shell silica particles are used as a stationary phase for chromatographic analysis using Kinetex® 2.6 μm Biphenyl LC Column, 4.6×50 mm, 2.6 μm. The mobile phase is a methanol-water mixture containing ~0.1% o-phosphoric acid (3:97 v/v Methanol). Quantitation of PEP is accomplished by comparing corresponding peak areas from the sample solution chromatogram and the Phenylephrine Hydrochloride Reference Standard (RS) solution.

Related substances: Determination of PEP related compounds is performed using a linear-gradient reversed-phase HPLC-UV method. Biphenyl-modified core-shell silica particles are used as stationary phase for chromatographic analysis using Kinetex®; Biphenyl LC Column, 4.6×150 mm, 2.6 μm. The mobile phase is prepared by online mixing of water with methanol with both solvents containing orthophosphoric acid. Related compounds are defined by their relative retention times (RRT). Quantitation of the related compounds is accomplished by comparing the corresponding peak areas from the Sample Solution chromatogram to the PEP peak area from the Phenylephrine Hydrochloride Reference Standard (RS) solution chromatogram. Relative response factors are used to correct for chemical structure effects on chromatographic responses.

As already mentioned above, the ionization behavior of phenylephrine and salts thereof in aqueous solution is fairly complex, with pKa values of about 9.07, 9.69 and greater than 14. These values correspond to ionization of the first phenolic group, amine group, and the benzylic hydroxyl group, respectively. In view of these data, it is therefore contemplated that pH values of less than 6.0 should be employed to prevent phenylephrine cyclization reaction. To that end and to verify pH ranges of between pH 5.0 and 6.0, the stability of exemplary phenylephrine HCl solution at 160 mcg/mL was tested at two different pH values, pH 5.0 and 6.0.

To determine the optimum pH, a pH-dependent stability study was conducted only at accelerated condition of 80° C. Phenylephrine hydrochloride solution, 400 mcg/mL was screened at five different pH conditions: 4.0, 4.5, 5.0, 5.5 and 6.0, and the compositions are shown in Table 2. Drug product was filled in 100 mL IV bags and terminally sterilized at 121° C. for 15 minutes. The IV bag was overwrapped with an aluminum overwrap with an oxygen scavenger. The initial time point was analyzed prior to and post terminal sterilization. Result are presented in Tables 3-7. The total impurities observed were lowest at pH 4.0 after 3 weeks at 80 C, 10-15% lower than at pH 4.5. There was no significant difference between the data at pH 4.5 and 5.0. Higher levels of total impurities were observed at pH 5.5 and 6.0. Since the product will be administered without dilution by intravenous route, though pH 4.0 formulation showed 10-15% less total impurities, pH 5.0 was selected to avoid any tolerability issues.

TABLE 2

Table 2: Composition of Phenylephrine Hydrochloride Solution, 400 mcg/mL at different pH conditions

| Ingredient | Quantity (mg/mL) | | | | |
| --- | --- | --- | --- | --- | --- |
| | Lot # 12136-A | Lot # 12136-B | Lot # 12136-C | Lot # 12136-D | Lot # 12136-E |
| Phenylephrine HCl | 0.4 | 0.4 | 0.4 | 0.4 | 0.4 |
| EDTA | 0.01 | 0.01 | 0.01 | 0.01 | 0.01 |
| Citric Acid | 1.05 | 1.05 | 1.05 | 1.05 | 1.05 |
| Sodium Chloride | 8.45 | 8.45 | 8.45 | 8.45 | 8.45 |
| 10N NaOH/6N HCl | q.s. to pH 4.0 | q.s. to pH 4.5 | q.s. to pH 5.0 | q.s. to pH 5.5 | q.s. to pH 6.0 |
| Water | q.s. to 1.0 mL | q.s. to 1.0 mL | q.s. to 1.0 mL | q.s. to 1.0 mL | q.s. to 1.0 mL |

TABLE 3

Table 3: Stability of Phenylephrine Hydrochloride Solution, 400 mcg/mL at pH 4.0 in citrate buffer.

| | | | Storage Condition | | |
| --- | --- | --- | --- | --- | --- |
| | | T0 | T0 | 80° C. | |
| Time Point | | (Pre-Sterilization) | (Autoclaved) | 3 days (Autoclaved) | 3 weeks (Autoclaved) |
| Appearance | | CCS | CCS | CCS | CCS |
| pH | | 4.02 | 3.96 | 3.97 | 4.04 |
| Assay (%) | | 101.2 | 101.7 | 101.5 | 102.8 |
| Related Compounds (%) | Unknown$_{(RRT)}$ | NR | NR | NR$_{(0.70)}$ 0.05$_{(0.73)}$ 0.07$_{(2.63)}$ 0.07$_{(2.25)}$ | 0.29$_{(0.66)}$ 0.19$_{(0.70)}$ 0.15$_{(1.55)}$ 0.05$_{(1.69)}$ 0.06$_{(1.80)}$ NR$_{(1.85)}$ 0.11$_{(2.21)}$ |
| | Total Impurities (%) | NR | NR | 0.19 | 0.85 |

CCS—Clear colorless solution;
NR—Not Reported (<0.05%)

TABLE 4

Table 4: Stability of Phenylephrine Hydrochloride Solution, 400 mcg/mL at pH 4.5 in citrate buffer.

| | | | Storage Condition | | |
| --- | --- | --- | --- | --- | --- |
| | | T0 | T0 | 80° C. | |
| Time Point | | (Pre-Sterilization) | (Autoclave) | 3 days | 3 weeks |
| Appearance | | CCS | CCS | CCS | CCS |
| pH | | 4.52 | 4.44 | 4.46 | 4.54 |
| Assay (%) | | 101.8 | 102.5 | 101.4 | 101.7 |
| Related Compounds (%) | Unknown$_{(RRT)}$ | NR | NR | NR | 0.27$_{(0.66)}$ 0.26$_{(0.70)}$ 0.14$_{(1.55)}$ 0.05$_{(1.69)}$ 0.08$_{(1.80)}$ 0.06$_{(1.85)}$ NR$_{(1.90)}$ 0.14$_{(2.21)}$ |
| | Total Impurities (%) | NR | NR | NR | 1.00 |

CCS—Clear colorless solution;
NR—Not Reported (<0.05%)

TABLE 5

Table 5: Stability of Phenylephrine Hydrochloride Solution, 400 mcg/mL at pH 5.0 in citrate buffer.

| | | | Storage Condition | | |
| --- | --- | --- | --- | --- | --- |
| | | T0 | T0 | 80° C. | |
| Time Point | | (Pre-Sterilization) | (Autoclave) | 3 days | 3 weeks |
| Appearance | | CCS | CCS | CCS | CCS |
| pH | | 5.01 | 4.98 | 4.98 | 4.98 |
| Assay (%) | | 102.2 | 101.5 | 100.7 | 102.8 |
| Related Compounds (%) | Unknown$_{(RRT)}$ | NR | NR | NR | 0.28$_{(0.66)}$ 0.27$_{(0.70)}$ 0.10$_{(1.55)}$ NR$_{(1.60)}$ |

TABLE 5-continued

Table 5: Stability of Phenylephrine Hydrochloride
Solution, 400 mcg/mL at pH 5.0 in citrate buffer.

| | Storage Condition | | | |
|---|---|---|---|---|
| | T0 | T0 | 80° C. | |
| Time Point | (Pre-Sterilization) | (Autoclave) | 3 days | 3 weeks |
| | | | | $0.06_{(1.69)}$ |
| | | | | $0.07_{(1.80)}$ |
| | | | | $0.05_{(1.85)}$ |
| | | | | $0.11_{(2.21)}$ |
| Total Impurities (%) | NR | NR | NR | 0.94 |

CCS—Clear colorless solution;
NR—Not Reported (<0.05%)

TABLE 6

Table 6: Stability of Phenylephrine Hydrochloride
Solution, 400 mcg/mL at pH 5.5 in citrate buffer.

| | | Storage Condition | | | |
|---|---|---|---|---|---|
| | | T0 | T0 | 80° C. | |
| Time Point | | (Pre-Sterilization) | (Autoclave) | 3 days | 3 weeks |
| Appearance | | CCS | CCS | CCS | CCS |
| pH | | 5.55 | 5.47 | 5.46 | 5.53 |
| Assay (%) | | 101.6 | 101.5 | 101.8 | 102.8 |
| Related Compounds (%) | Unknown$_{(RRT)}$ | NR | NR | NR | $0.49_{(0.66)}$ |
| | | | | | $0.24_{(0.70)}$ |
| | | | | | $0.08_{(1.55)}$ |
| | | | | | $0.05_{(1.60)}$ |
| | | | | | $0.07_{(1.69)}$ |
| | | | | | $0.08_{(1.80)}$ |
| | | | | | $0.05_{(1.85)}$ |
| | | | | | $0.12_{(2.21)}$ |
| | | | | | NR$_{(2.90)}$ |
| | | | | | $0.06_{(3.20)}$ |
| | | | | | $0.05_{(4.13)}$ |
| Total Impurities (%) | | NR | NR | NR | 1.29 |

CCS—Clear colorless solution;
NR—Not Reported (<0.05%)

TABLE 7

Table 7: Stability of Phenylephrine Hydrochloride
Solution, 400 mcg/mL at pH 6.0 in citrate buffer.

| | | Storage Condition | | | |
|---|---|---|---|---|---|
| | | T0 | T0 | 80° C. | |
| Time Point | | (Pre-Sterilization) | (Autoclave) | 3 days | 3 weeks |
| Appearance | | CCS | CCS | CCS | CCS |
| pH | | 5.99 | 5.97 | 5.97 | 6.00 |
| Assay (%) | | 101.4 | 100.9 | 100.4 | 102.7 |
| Related Compounds (%) | Unknown (RRT) | NR | NR | NR$_{(1.73)}$ | $0.50_{(0.66)}$ |
| | | | | NR$_{(1.80)}$ | $0.12_{(0.70)}$ |
| | | | | $0.19_{(1.94)}$ | NR$_{(1.60)}$ |
| | | | | | $0.07_{(1.69)}$ |
| | | | | | $0.08_{(1.80)}$ |
| | | | | | $0.05_{(1.85)}$ |
| | | | | | $0.39_{(1.90)}$ |
| | | | | | $0.12_{(2.21)}$ |

TABLE 7-continued

Table 7: Stability of Phenylephrine Hydrochloride Solution, 400 mcg/mL at pH 6.0 in citrate buffer.

| | Storage Condition | | | |
|---|---|---|---|---|
| | T0 | T0 | 80° C. | |
| Time Point | (Pre-Sterilization) | (Autoclave) | 3 days | 3 weeks |
| | | | | $0.21_{(2.90)}$ |
| | | | | $0.09_{(3.20)}$ |
| | | | | $NR_{(4.13)}$ |
| Total Impurities (%) | NR | NR | 0.19 | 1.63 |

CCS—Clear colorless solution;
NR—Not Reported (<0.05%)

Selection of buffering agent: Based on the pH screening study, a pH of 5.0 was selected as the target pH. Since phenylephrine hydrochloride does not have a pKa within one unit of pH 5.0, a buffering agent was necessary to maintain the pH of the drug product over the shelf-life.

A buffering agent is a weak acid or base used to maintain the pH of a solution near a chosen value after the addition of another acid or base. That is, the function of a buffering agent is to prevent a rapid change in pH when acids or bases are added to the solution. Buffer concentration and buffer selection play an important role in maintaining the pH of the product. It is generally advised to choose a buffering agent whose pKa is close to the pH of the product. Citric acid (pKa—3.1, 4.7, and 6.4), tartaric acid (pKa—2.98, 4.34) and acetic acid (pKa—4.76) were chosen as buffering agents for the stability study.

Stability of Phenylephrine hydrochloride solution, 400 mcg/mL was tested in 5 mM citrate acid, acetic acid and tartaric acid at two different conditions (60° C. and 80°). The composition for the study is presented in Table 8. The drug product was filled in 100 mL IV bags and sterilized at 121° C. for 15 minutes. Bags were overwrapped with an aluminum overwrap with an oxygen scavenger. Samples were tested for appearance, pH, color change, assay, and related substances at different time points. Based on the data, it was observed that the degradation of Phenylephrine hydrochloride was the least in acetic acid followed by citric acid and tartaric acid at 60° C. at 3 weeks. Hence, acetic was chosen as the primary buffer and citric acid was chosen as a back-up buffer to in the next study to determine effect of buffer concentration. Exemplary results are presented in Tables 9-11.

TABLE 8

Table 8: Composition of Phenylephrine Hydrochloride Solution, 400 mcg/mL with different buffers

| | Quantity (mg/mL) | | |
|---|---|---|---|
| Ingredient | Lot # 12206 (5 mM Citrate buffer) | Lot # 12207 (5 mM Acetate buffer) | Lot # 12208 (5 mM Tartrate buffer) |
| Phenylephrine HCl | 0.4 | 0.4 | 0.4 |
| Acetic Acid | — | 0.3 | — |
| Citric Acid | 1.05 | — | — |
| Tartaric Acid | — | — | 0.75 |
| Sodium Chloride | 8.55 | 8.3 | 8.17 |
| 10N NaOH/6N HCl | q.s. to pH 5.0 | q.s. to pH 5.0 | q.s. to pH 5.0 |
| Water | q.s. to 1.0 mL | q.s. to 1.0 mL | q.s. to 1.0 mL |

TABLE 9

Table 9: Stability of Phenylephrine Hydrochloride Solution, 400 mcg/mL in 5 mM Citrate buffer at pH 5.0.

| | | Storage Condition | | | | | |
|---|---|---|---|---|---|---|---|
| | | | 60° C. | | | 80° C. | |
| Time Point | Initial | Day 4 | 1 week | 3 week | Day 4 | 1 week | 3 week |
| Appearance | CCS | CCS | CCS | CCS | CCS | CCS | CCS |
| pH | 5.01 | 5.00 | 4.99 | 4.96 | 5.01 | 4.99 | 4.97 |
| Assay (%) | 99.2 | 98.8 | 99.0 | 98.8 | 99.1 | 98.7 | 100.1 |
| Impurity C | NR | NR | NR | 0.11 | NR | NR | 0.10 |
| Impurity E | NR | NR | NR | NR | NR | NR | 0.16 |
| Impurity F | NR | NR | NR | 0.06 | NR | NR | NR |
| Related Unknown$_{(RRT)}$ | $NR_{(0.61)}$ | $NR_{(0.61)}$ | $NR_{(1.80)}$ | $NR_{(0.90)}$ | $NR_{(0.70)}$ | $NR_{(1.69)}$ | $0.32_{(0.70)}$ |

TABLE 9-continued

Table 9: Stability of Phenylephrine Hydrochloride Solution, 400 mcg/mL in 5 mM Citrate buffer at pH 5.0.

| | | Storage Condition | | | | | |
|---|---|---|---|---|---|---|---|
| | | 60° C. | | | 80° C. | | |
| Time Point | Initial | Day 4 | 1 week | 3 week | Day 4 | 1 week | 3 week |
| Compounds (%) | $0.09_{(0.70)}$ $NR_{(1.69)}$ $NR_{(1.80)}$ $0.07_{(2.21)}$ $0.07_{(4.13)}$ | $NR_{(0.70)}$ $0.09_{(4.13)}$ | $0.05_{(0.70)}$ | $0.23_{(1.16)}$ $NR_{(1.23)}$ $0.28_{(1.60)}$ $NR_{(1.69)}$ $NR_{(1.83)}$ $NR_{(1.85)}$ $NR_{(1.90)}$ $0.16_{(2.21)}$ $0.05_{(2.53)}$ | $0.07_{(4.13)}$ | $NR_{(1.80)}$ $NR_{(1.85)}$ $0.14_{(0.70)}$ $0.06_{(2.21)}$ | $0.1_{(1.55)}$ $0.18_{(1.60)}$ $NR_{(1.69)}$ $0.06_{(1.83)}$ $NR_{(1.85)}$ $0.07_{(2.21)}$ $0.05_{(4.13)}$ |
| Total Impurities (%) | 0.23 | 0.09 | 0.05 | 0.89 | 0.07 | 0.20 | 1.04 |

CCS—Clear colorless solution;
NR—Not Reported (<0.05%)

TABLE 10

Table 10: Stability of Phenylephrine Hydrochloride Solution, 400 mcg/mL in 5 mM acetate buffer at pH 5.0.

| | | Storage Condition | | | | | |
|---|---|---|---|---|---|---|---|
| | | 60° C. | | | 80° C. | | |
| Time Point | Initial | Day 4 | 1 week | 3 week | Day 4 | 1 week | 3 week |
| Appearance | CCS | CCS | CCS | CCS | CCS | CCS | CCS |
| pH | 5.02 | 5.02 | 4.99 | 4.98 | 5.04 | 5.00 | 5.00 |
| Assay (%) | 101.5 | 99.7 | 101.5 | 101.8 | 100.5 | 100.8 | 102.8 |
| Impurity C | NR | NR | NR | 0.12 | NR | NR | 0.13 |
| Impurity E | NR | NR | NR | NR | NR | NR | 0.12 |
| Related Compounds (%) Unknown$_{(RRT)}$ | NR | NR | $NR_{(2.21)}$ $0.09_{(4.13)}$ | $NR_{(0.90, 1.22; 1.55)}$ $0.08_{(1.60)}$ $0.12_{(1.73)}$ $NR_{(1.83)}$ $NR_{(1.85)}$ $0.09_{(2.21)}$ $NR_{(2.76)}$ $NR_{(4.13)}$ | $NR_{(2.21,)}$ $NR_{(2.76)}$ $0.05_{(4.13)}$ | $NR_{(1.55)}$ $NR_{(1.69)}$ $NR_{(1.80)}$ $NR_{(1.85)}$ $0.07_{(2.21)}$ | $0.10_{(1.16)}$ $0.17_{(1.60)}$ $NR_{(1.69, 1.83)}$ $0.05_{(1.85)}$ $NR_{(1.90)}$ $0.23_{(2.21)}$ $0.1_{(3.20)}$ |
| Total (%) | NR | NR | 0.09 | 0.41 | 0.05 | 0.07 | 0.90 |

CCS—Clear colorless solution;
NR—Not Reported (<0.05%)

TABLE 11

Table 11: Stability of Phenylephrine Hydrochloride Solution, 400 mcg/mL in 5 mM tartrate buffer at pH 5.0.

| | | Storage Condition | | | | | |
|---|---|---|---|---|---|---|---|
| | | 60° C. | | | 80° C. | | |
| Time Point | Initial | Day 4 | 1 week | 3 week | Day 4 | 1 week | 3 week |
| Appearance | CCS | CCS | CCS | CCS | CCS | CCS | CCS |
| pH | 5.02 | 5.02 | 5.03 | 5.03 | 5.08 | 5.04 | 5.02 |
| Assay (%) | 98.9 | NT | 98.7 | 99.1 | 98.3 | 98.8 | 99.1 |
| Impurity C | NR | NT | NR | 0.15 | NR | NR | 0.08 |
| Impurity D | NR | NT | NR | 0.08 | NR | NR | NR |
| Impurity E | NR | NT | NR | NR | 0.05 | NR | NR |
| Related Compounds (%) Unknown$_{(RRT)}$ | NR | NT | NR | $0.22_{(0.70)}$ $0.19_{(1.55)}$ $NR_{(1.80)}$ | $NR_{(1.73)}$ $NR_{(1.80)}$ $NR_{(1.88)}$ | $0.05_{(1.60)}$ $NR_{(1.69)}$ $NR_{(1.80)}$ | $0.10_{(1.16)}$ $0.06_{(1.23)}$ $NR_{(1.55)}$ |

TABLE 11-continued

Table 11: Stability of Phenylephrine Hydrochloride Solution, 400 mcg/mL in 5 mM tartrate buffer at pH 5.0.

| | | Storage Condition | | | | | |
|---|---|---|---|---|---|---|---|
| | | 60° C. | | | 80° C. | | |
| Time Point | Initial | Day 4 | 1 week | 3 week | Day 4 | 1 week | 3 week |
| | | | | $0.12_{(1.85)}$ | $0.10_{(2.21)}$ | $NR_{(1.85)}$ | $NR_{(1.60)}$ |
| | | | | $0.11_{(2.21)}$ | $0.10_{(2.53)}$ | $0.08_{(2.21)}$ | $0.07_{(1.69)}$ |
| | | | | $0.19_{(2.25)}$ | $NR_{(2.76)}$ | $NR_{(2.53)}$ | $0.05_{(1.83)}$ |
| | | | | $NR_{(3.20)}$ | | | $0.12_{(2.21)}$ |
| | | | | $NR_{(3.38)}$ | | | $0.06_{(3.20)}$ |
| | | | | $0.10_{(4.13)}$ | | | |
| Total (%) | NR | NT | NR | 1.16 | 0.25 | 0.13 | 0.62 |

CCS—Clear colorless solution;
NR—Not Reported (<0.05%),
NT—Not Tested

Buffer Concentration: Stability of phenylephrine hydrochloride was determined at 1 mM and 2 mM citrate buffer and compared to stability of 5 mM acetate buffer. Stability of phenylephrine hydrochloride solution was bracketed at 40 mcg/mL and 400 mcg/mL. The formulation compositions for the study are shown in Table 12. Drug product was filled in 100 mL IV bag and terminally sterilized at 121° C. for 15 minutes. The sterilized bag was then encased in an aluminum overwrap with an oxygen scavenger. Stability testing was carried out at 25° C./60% RH and 40° C./75% RH. The samples were tested for appearance, pH, dissolved oxygen, color change, assay and related substances at different time points. Based on the results, it was observed that phenylephrine hydrochloride was more stable in 5 mM acetic acid than in 1 mM and 2 mM citric acid at the same pH as can be seen from the results in Tables 13-18.

TABLE 12

Table 12: Compositions of Phenylephrine Hydrochloride Solution, 40 mcg/mL and 400 mcg/mL in acetate and citrate buffer.

| | Quantity (mg/mL) | | | | | |
|---|---|---|---|---|---|---|
| | 5 mM Acetate Buffer | | 1 mM Citrate | | 2 mM Citrate | |
| Ingredients | Lot # 12323 | Lot # 12322 | Lot # 12457 | Lot # 12382 | Lot # 12458 | Lot # 12381 |
| Phenylephrine HCl | 0.04 | 0.4 | 0.04 | 0.4 | 0.04 | 0.4 |
| Glacial acetic acid | 0.3 | 0.3 | — | — | — | — |
| Citric acid | — | — | 0.21 | 0.21 | 0.42 | 0.42 |
| Sodium Chloride | 8.46 | 8.30 | 8.73 | 8.57 | 8.70 | 8.54 |
| 10N NaOH/6N HCl | q.s to pH 5.0 | q.s to pH 5.0 | q.s to pH 5.0 | q.s to pH 5.0 | q.s to pH 5.0 | q.s to pH 5.0 |
| Water | q.s. 1.0 mL | q.s. 1.0 mL | q.s. 1.0 mL | q.s. 1.0 mL | q.s. 1.0 mL | q.s. 1.0 mL |

TABLE 13

Table 13: Stability of Phenylephrine Hydrochloride Solution, 40 mcg/mL in 5 mM acetate buffer at pH 5.0.

| | | Storage Condition | | | | | | | |
|---|---|---|---|---|---|---|---|---|---|
| | | 25° C. ± 2° C./60% RH ± 5% RH | | | | 40 ± 2° C./75 ± 5% RH | | | |
| Time Point | Initial | 1 M | 2 M | 3 M | 6 M | 1 M | 2 M | 3 M | 6 M |
| Appearance | CCS | CCS | CCS | CCS | CCS | CCS | CCS | CCS | CCS |
| Assay (%) | 100.4 | 100.5 | 101.5 | 102.4 | 101.3 | 100.6 | 101.5 | 102.9 | 101.9 |
| Dissolved oxygen (ppm) | NT | 1.24 | 1.53 | 1.84 | 1.21 | 1.50 | 0.89 | 1.72 | 2.15 |

TABLE 13-continued

Table 13: Stability of Phenylephrine Hydrochloride Solution, 40 mcg/mL in 5 mM acetate buffer at pH 5.0.

| | | Storage Condition | | | | | | | | |
|---|---|---|---|---|---|---|---|---|---|---|
| | | 25° C. ± 2° C./60% RH ± 5% RH | | | | | 40 ± 2° C./75 ± 5% RH | | | |
| Time Point | Initial | 1 M | 2 M | 3 M | 6 M | 1 M | 2 M | 3 M | 6 M |
| pH | NT | 5.00 | 5.00 | 5.04 | 5.01 | 5.03 | 5.00 | 5.04 | 5.08 |
| Impurity C* | NR | NR | NR | NR | NR | NR | NR | NR | 0.07 |
| Impurity F** | NR | 0.09 | NR | 0.1 | 0.12 | 0.11 | NR | 0.06 | 0.08 |
| Related Unknown$_{(RRT)}$ Substance (%) | NR | 0.06$_{(1.45)}$ NR$_{(2.00)}$ NR$_{(2.60)}$ NR$_{(2.84)}$ | 0.07$_{(0.73)}$ | 0.06$_{(1.53)}$ NR$_{(3.16)}$ | NR | 0.06$_{(1.45)}$ NR$_{(1.60)}$ 0.06$_{(2.40)}$ 0.07$_{(2.64)}$ NR$_{(3.60)}$ | NR | NR$_{(1.70)}$ NR$_{(1.86)}$ NR$_{(1.95)}$ NR$_{(2.0)}$ NR$_{(1.53)}$ | 0.06$_{(1.70)}$ 0.06$_{(1.9)}$ 0.36$_{(2.42)}$ 0.07$_{(2.82)}$ 0.10$_{(3.58)}$ |
| Total (%) | NR | 0.15 | 0.07 | 0.16 | 0.12 | 0.30 | NR | 0.07 | 0.34 |

*Impurity F - 2-Methyl-1,2,3,4-tetrahydroisoquinoline-4,8-diol;
**Impurity C- 1-(3-Hydroxyphenyl)-2-(methylamino)ethan-1-one hydrochloride (Phenylephrone - phenylephrine related compound);
CCS—Clear colorless solution;
NR—Not Reported (<0.05%);
NT—Not tested

TABLE 14

Table 14: Stability of Phenylephrine Hydrochloride Solution, 400 mcg/mL in 5 mM acetate buffer at pH 5.0.

| | | Storage Condition | | | | | | | | |
|---|---|---|---|---|---|---|---|---|---|---|
| | | 25° C. ± 2° C./60% RH ± 5% RH | | | | | 40 ± 2° C./75 ± 5% RH | | | |
| Time Point | Initial | 1 M | 2 M | 3 M | 6 M | 1 M | 2 M | 3 M | 6 M |
| Appearance | CCS | CCS | CCS | CCS | CCS | CCS | CCS | CCS | CCS |
| Assay (%) | 99.5 | 101.2 | 100.4 | 102.8 | 101.0 | 100.9 | 100.6 | 102.2 | 100.6 |
| Dissolved oxygen (ppm) | N/A | 0.98 | 1.05 | 1.76 | 1.46 | 1.18 | 1.03 | 1.83 | 1.77 |
| pH | N/A | 5.03 | 5.05 | 5.06 | 4.99 | 5.05 | 5.05 | 5.05 | 5.01 |
| Impurity F* | NR | NR | NR | NR | NR | NR | NR | NR | NR |
| Related Unknown$_{(RRT)}$ Substance (%) | NR | NR | NR | NR | NR | NR | NR | NR$_{(1.86)}$ NR$_{(2.0)}$ NR$_{(3.0)}$ | NR |
| Total (%) | NR | NR | NR | NR | NR | NR | NR | NR | NR |

*Impurity F - 2-Methyl-1,2,3,4-tetrahydroisoquinoline-4,8-diol;
CCS—Clear colorless solution;
NR—Not Reported (<0.05%).

TABLE 15

Table 15: Stability of Phenylephrine Hydrochloride Solution, 40 mcg/mL in 1 mM citrate buffer at pH 5.0.

| | | Storage Condition | | | | | | | | |
|---|---|---|---|---|---|---|---|---|---|---|
| | | 25° C. ± 2° C./60% RH ± 5% RH | | | | | 40 ± 2° C./75 ± 5% RH | | | |
| Time Point | Initial | 1 Month | 2 Month | 3 Month | 6 Month | 1 Month | 2 Month | 3 Month | 6 Month |
| Appearance | CCS | CCS | CCS | CCS | CCS | CCS | CCS | CCS | CCS |
| Assay (%) | 100.4 | 100.1 | 100.9 | 100.8 | 102.5 | 100.1 | 100.9 | 101.0 | 102.5 |
| Dissolved oxygen (ppm) | NT | 1.5 | 1.38 | 1.68 | 1.58 | 1.24 | 2.81 | 1.18 | 1.41 |
| pH | NT | 5.01 | 5.02 | 5.02 | 5.08 | 5.04 | 5.01 | 5.01 | 5.1 |
| Impurity F | NR | NR | NR | NR | 0.26 | 0.14 | NR | NR | 0.28 |
| Impurity C | NR | NR | NR | NR | 0.19 | NR | NR | NR | 0.2 |
| Impurity G | NR | NR | NR | NR | 0.07 | NR | NR | NR | 0.07 |
| Related Unknown$_{(RRT)}$ Compounds (%) | NR | 0.05$_{(0.73)}$ NR$_{(2.68)}$ | NR | NR$_{(1.60)}$ | NR | 0.11$_{(0.60)}$ NR$_{(0.80)}$ 0.05$_{(1.75)}$ | NR | 0.17$_{(2.60)}$ 0.21$_{(1.60)}$ 0.25$_{(1.75)}$ | 0.29$_{(9.18)}$ |

TABLE 15-continued

Table 15: Stability of Phenylephrine Hydrochloride Solution, 40 mcg/mL in 1 mM citrate buffer at pH 5.0.

| | Storage Condition | | | | | | | | |
|---|---|---|---|---|---|---|---|---|---|
| | 25° C. ± 2° C./60% RH ± 5% RH | | | | | 40 ± 2° C./75 ± 5% RH | | | |
| Time Point | Initial | 1 Month | 2 Month | 3 Month | 6 Month | 1 Month | 2 Month | 3 Month | 6 Month |
| | | | | | | $0.05_{(2.68)}$ | | $NR_{(2.68)}$ | |
| | | | | | | | | $NR_{(1.85)}$ | |
| | | | | | | | | $NR_{(2.0)}$ | |
| | | | | | | | | $NR_{(2.1)}$ | |
| | | | | | | | | $NR_{(2.85)}$ | |
| Total (%) | NR | 0.05 | NR | NR | 0.8 | 0.30 | NR | 0.63 | NR |

CCS—Clear colorless solution;
NR—Not Reported (0.05%),
NT—Not Tested

TABLE 16

Table 16: Stability of Phenylephrine Hydrochloride Solution, 400 mcg/mL in 1 mM citrate buffer at pH 5.0.

| | Storage Condition | | | | | | | | |
|---|---|---|---|---|---|---|---|---|---|
| | 25° C. ± 2° C./60% RH ± 5% RH | | | | | 40 ± 2° C./75 ± 5% RH | | | |
| Time Point | Initial | 1 Month | 2 Month | 3 Month | 6 Month | 1 Month | 2 Month | 3 Month | 6 Month |
| Appearance | CCS | CCS | CCS | CCS | CCS | CCS | CCS | CCS | CCS |
| Assay (%) | 100.6 | 99.6 | 100.7 | 101.5 | 100.0 | 100.0 | 101.5 | 102.8 | 102.7 |
| Dissolved oxygen (ppm) | NT | 1.34 | 2.00 | 2.18 | 7.06 | 1.79 | 1.28 | 1.7 | 1.09 |
| pH | NT | 5.05 | 4.98 | 5.03 | 4.95 | 5.05 | 4.99 | 5.03 | 4.96 |
| Impurity F | NR | NR | NR | NR | 0.06 | NR | NR | NR | NR |
| Impurity C | NR | NR | NR | NR | 0.07 | NR | NR | NR | NR |
| Impurity G | NR | NR | NR | NR | 0.08 | NR | NR | NR | NR |
| Related Unknown$_{(RRT)}$ Compounds (%) | NR | NR | NR | NR | $0.32_{(0.49)}$ $0.12_{(0.78)}$ $0.35_{(1.78)}$ $0.06_{(1.96)}$ $0.09_{(2.82)}$ $0.03_{(3.57)}$ | NR | NR | $NR_{(1.70)}$ $NR_{(1.86)}$ $NR_{(1.95)}$ $NR_{(2.0)}$ | NR |
| Total (%) | NR | NR | NR | NR | 0.97 | NR | NR | NR | NR |

CCS—Clear colorless solution;
NR—Not Reported (<0.05%),
NT—Not Tested

TABLE 17

Table 17: Stability of Phenylephrine Hydrochloride Solution, 40 mcg/mL in 2 mM citrate buffer at pH 5.0.

| | | | 25° C. ± 2° C./ 60% RH ± 5% RH | | | | 40 ± 2° C./ 75 ± 5% RH | | | |
|---|---|---|---|---|---|---|---|---|---|---|
| Time Point | | Initial | 1 Month | 2 Month | 3 Month | 6 Month | 1 Month | 2 Month | 3 Month | 6 Month |
| Appearance | | CCS | CCS | CCS | CCS | CCS | CCS | CCS | CCS | CCS |
| Assay (%) | | 100.2 | 100.2 | 100.9 | 101.0 | 102.4 | 100.0 | 101.0 | 101.4 | 101.8 |
| Dissolved oxygen (ppm) | | NT | 1.18 | 4.97 | 1.67 | 4.96 | 0.98 | 4.95 | 1.62 | 2.25 |
| pH | | NT | 4.99 | 1.75 | 4.98 | 1.52 | 5.00 | 1.9 | 4.98 | 5.07 |
| Impurity F | | 0.10 | NR | NR | NR | 0.12 | 0.11 | NR | NR | 0.08 |
| Impurity C | | NR | NR | NR | NR | 0.10 | NR | NR | NR | 0.07 |
| Impurity G | | NR | NR | NR | NR | NR | NR | NR | NR | 0.03 |
| Related Compounds (%) | Unknown$_{(RRT)}$ | 0.07$_{(0.70)}$ NR$_{(0.73)}$ NR$_{(1.45)}$ 0.07$_{(3.60)}$ | NR$_{(0.73)}$ NR$_{(3.0)}$ | NR | 0.06$_{(1.60)}$ 0.05$_{(1.75)}$ NR$_{(2.60)}$ NR$_{(2.68)}$ | NR | 0.11$_{(1.60)}$ 0.05$_{(0.73)}$ NR$_{(1.80)}$ 0.05$_{(2.68)}$ NR$_{(3.0)}$ | NR | 0.15$_{(2.6)}$ 0.05$_{(1.60)}$ 0.05$_{(1.75)}$ NR$_{(1.80)}$ NR$_{(2.68)}$ | 0.29$_{(2.42)}$ 0.07$_{(2.82)}$ 0.11$_{(3.57)}$ 0.28$_{(9.18)}$ NR$_{(1.7)}$ |
| Total (%) | | 0.24 | NR | NR | 0.11 | 0.22 | 0.32 | NR | 0.25 | 0.68 |

CCS—Clear colorless solution;
NR—Not Reported (<0.05%),
NT—Not Tested

TABLE 18

Table 18: Stability of Phenylephrine Hydrochloride Solution, 400 mcg/mL in 2 mM citrate buffer at pH 5.0.

| | | | 25° C. ± 2° C./ 60% RH ± 5% RH | | | | 40 ± 2° C./ 75 ± 5% RH | | | |
|---|---|---|---|---|---|---|---|---|---|---|
| Time Point | | Initial | 1 Month | 2 Month | 3 Month | 6 Month | 1 Month | 2 Month | 3 Month | 6 Month |
| Appearance | | CCS | CCS | CCS | CCS | CCS | CCS | CCS | CCS | CCS |
| Assay (%) | | 100.9 | 100.8 | 101.2 | 101.9 | 102.4 | 100.7 | 102.2 | 102.0 | 101.6 |
| Dissolved oxygen (ppm) | | NT | 1.35 | 2.04 | 2.51 | 1.67 | 1.48 | 1.84 | 1.92 | 1.09 |
| pH | | NT | 5.08 | 4.98 | 5.04 | 4.95 | 5.06 | 4.99 | 5.05 | 4.97 |
| Impurity F | | NR | NR | NR | NR | NR | NR | NR | NR | NR |
| Related Compounds (%) | Unknown$_{(RRT)}$ | NR | NR$_{(3.44)}$ | NR | NR | NR | NR | NR | NR$_{(1.86)}$ NR$_{(1.95)}$ | NR |
| | Total Impurities (%) | NR | NR | NR | NR | NR | NR | NR | NR | NR |

CCS—Clear colorless solution;
NR—Not Reported (<0.05%),
NT—Not Tested

The above studies to screen the types of buffer and their optimum concentration were all conducted by filling the formulation in 100 mL polypropylene bags from Technoflex. These polypropylene bags were part of the primary packaging component of the product. The filled bags (primary packaging) were further packaged into an aluminum overwrap pouch with an oxygen scavenger (secondary packaging). According to literature studies and data from initial studies suggested that phenylephrine hydrochloride was comparatively stable to oxidative degradation to its sympathomimetic amine counterparts. Hence, a study was conducted to evaluate the necessity of oxygen scavenger to product stability.

Stability of Phenylephrine hydrochloride solution, 40 mcg/mL and 400 mcg/mL were tested at 1 mM, 2 mM and 5 mM acetate buffer with secondary aluminum overwrap without an oxygen scavenger. The samples as shown in Table 19 were tested for appearance, pH, assay, and related substances at different time points. Based on the results shown in Tables 20-25, it was observed that the formulation with 5 mM acetate buffer was more stable and had less degradation compared to 1 mM and 2 mM acetate buffer.

TABLE 19

Table 19: Composition of Phenylephrine Hydrochloride solution (40 mcg/mL and 400 mcg/mL) for secondary packaging evaluation

| | Quantity (mg/mL) | | | | | |
|---|---|---|---|---|---|---|
| | 5 mM Acetate buffer | | 1 mM Acetate buffer | | 2 mM Acetate buffer | |
| Ingredients | Lot #12857 | Lot #12849 | Lot #12943 | Lot #12968 | Lot #12944 | Lot #12969 |
| Phenylephrine HCl | 0.04 | 0.4 | 0.04 | 0.4 | 0.04 | 0.4 |
| Glacial acetic acid | 0.3 | 0.3 | 0.06 | 0.06 | 0.12 | 0.12 |
| Sodium Chloride | 8.46 | 8.46 | 8.73 | 8.3 | 8.46 | 8.3 |
| 10N NaOH/6N HCl | q.s to pH 5.0 | q.s to pH 5.0 | q.s to pH 5.0 | q.s to pH 5.0 | q.s to pH 5.0 | q.s to pH 5.0 |
| Water | q.s. 1 mL | q.s. 1 mL | q.s. 1 mL | q.s. 1 mL | q.s. 1 mL | q.s. 1 mL |

TABLE 20

Table 20: Stability of Phenylephrine Hydrochloride solution, 40 mcg/mL in 5 mM acetate buffer with aluminum overwrap.

| | | | Time point | | | | |
|---|---|---|---|---|---|---|---|
| | | | 1 Month | 3 Month | | 6 Month | |
| Storage Condition | Initial | 3 Weeks 60° C. | 40 ± 2° C./ 75 ± 5% RH | 25° C. ± 2° C./ 60% RH ± 5% RH | 40 ± 2° C./ 75 ± 5% RH | 25° C. ± 2° C./ 60% RH ± 5% RH | 40 ± 2° C./ 75 ± 5% RH |
| Appearance | CCS | CCS | CCS | CCS | CCS | CCS | CCS |
| Assay (%) | 100.4 | 102.2 | 100.8 | 101.7 | 101.4 | 101.4 | 101.0 |
| pH | 4.91 | 5.12 | 4.91 | 4.93 | 4.9 | 4.88 | 4.89 |
| Impurity F | NR | NR | 0.08 | 0.08 | 0.08 | 0.06 | 0.14 |
| Impurity C | NR | NR | NR | 0.07 | 0.1 | NR | 0.09 |
| Related Unknown$_{(RRT)}$ Substance (%) | NR | 0.05$_{(1.45)}$ 0.05$_{(2.0)}$ NR$_{(3.0)}$ | 0.05$_{(3.0)}$ | NR | NR | NR | NR |
| Total (%) | NR | 0.05 | 0.13 | 0.15 | 0.18 | 0.06 | 0.23 |

CCS—Clear colorless solution;
NR—Not Reported (<0.05%),
NT—Not Tested

TABLE 21

Table 21: Stability of Phenylephrine Hydrochloride solution, 400 mcg/mL in 5 mM acetate buffer with aluminum overwrap.

| | | | Time point | | | | |
|---|---|---|---|---|---|---|---|
| | | | 1 Month | 3 Month | | 6 Month | |
| Storage Condition | Initial | 3 Weeks 60° C. | 40 ± 2° C./ 75 ± 5% RH | 25° C. ± 2° C./ 60% RH ± 5% RH | 40 ± 2° C./ 75 ± 5% RH | 25° C. ± 2° C./ 60% RH ± 5% RH | 40 ± 2° C./ 75 ± 5% RH |
| Appearance | CCS | CCS | CCS | CCS | CCS | CCS | CCS |
| Assay (%) | 99.1 | 102.2 | 99.7 | 102.5 | 101.5 | 100.2 | 99.2 |
| pH | 5.02 | 4.99 | 5.02 | 5.01 | 5.03 | 4.99 | 5.02 |
| Impurity F | NR | NR | NR | NR | NR | NR | 0.09 |
| Related Substance Unknown$_{(RRT)}$ | NR | NR | 0.08 | 0.08$_{(1.37)}$ | NR | NR | NR |
| (%) Total (%) | NR | NR | 0.08 | 0.08 | NR | NR | 0.09 |

CCS—Clear colorless solution;
NR—Not Reported (<0.05%),
NT—Not Tested.

TABLE 22

Table 22: Stability of Phenylephrine Hydrochloride Solution, 40 mcg/mL in 1 mM acetate buffer with aluminum overwrap.

| | | Storage Condition | | | | | | |
|---|---|---|---|---|---|---|---|---|
| | | 60° C. | | | 40 ± 2° C./ 75 ± 5% RH | | | |
| | | 2 Weeks | | | 1 Month | | 3 Month | |
| Time Point | Initial | S | NS | N | NS | N | NS | N |
| Appearance | CCS | CCS | BCS | BCS | BCS | BCS | BCS | BCS |
| Assay (%) | 100.2 | 101.9 | 46.8 | 43.1 | 99.5 | 97.6 | 69.7 | 57.5 |
| pH | 4.9 | 4.9 | 4.68 | 4.88 | 4.87 | 4.86 | 4.75 | 4.7 |
| IMP C | NR | NR | 2.12 | 1.93 | 0.19 | 0.35 | 1.97 | 1.9 |
| IMP F | 0.05 | 0.08 | 5.05 | 4.61 | 0.28 | 0.54 | 2.74 | 2.87 |
| IMP G | NR | NR | 0.09 | 0.08 | NR | NR | 0.06 | 0.08 |
| IMP D | NR | NR | 0.09 | NR | NR | NR | NR | NR |
| IMP A | NR | NR | NR | NR | NR | NR | 0.06 | 0.08 |
| Related Substance Unknown$_{(RRT)}$ (%) | 0.07 (3.0) | 0.17 (9.181) | 0.27 (1.451) 0.26 (1.597) 0.09 (1.654) 0.1 (3.588) 0.13 (5.67) 0.09 (5.828) 1.31 (6.426) 0.56 (6.875) 0.12 (7.007) 0.31 (7.152) 0.08 (7.49) 0.12 (7.771) 0.16 (8.411) 0.22 (9.181) 0.33 (9.959) | 0.37 (1.451) 0.32 (1.597) 0.13 (1.654) 0.12 (3.588) 0.09 (3.719) 0.09 (5.67) 0.07 (5.828) 2.1 (6.426) 0.83 (6.875) 0.13 (7.007) 0.49 (7.152) 0.15 (7.49) 0.14 (7.771) 0.11 (7.982) 0.21 (8.411) | 0.2 (1.78) 0.09 (1.965) 0.13 (3.037) | 0.94 (1.78) 0.15 (1.965) 0.13 (3.037) 0.06 (3.076) | 0.2 (0.488) 0.09 (0.53) 0.08 (0.784) 0.11 (0.888) 0.07 (1.231) 0.07 (1.376) 2.9 (1.78) 1.07 (1.965) 0.09 (2.021) 0.12 (2.059) 0.06 (2.334) 0.07 (2.347) 0.08 (2.48) 0.07 (2.667) 0.73 (2.825) | 0.27 (0.488) 0.16 (0.53) 0.14 (0.784) 0.14 (0.888) 0.07 (1.192) 0.1 (1.231) 0.06 (1.376) 0.06 (1.704) 2.08 (1.78) 1.18 (1.965) 0.18 (2.021) 0.1 (2.059) 0.09 (2.347) 0.08 (2.48) 0.06 (2.625) |

TABLE 22-continued

Table 22: Stability of Phenylephrine Hydrochloride Solution, 40 mcg/mL in 1 mM acetate buffer with aluminum overwrap.

|  |  |  |  | 0.09<br>(10.525)<br>0.1<br>(10.657)<br>1.4<br>(11.736) | 0.28<br>(9.181)<br>0.41<br>(9.959)<br>0.1<br>(10.525)<br>0.1<br>(10.657)<br>1.44<br>(11.736) |  |  | 0.14<br>(3.037)<br>0.11<br>(3.076)<br>0.17<br>(IMP 9) | 0.1<br>(2.667)<br>1.33<br>(2.825)<br>0.08<br>(3.037)<br>0.22<br>(3.076)<br>0.07<br>(3.188)<br>0.3<br>(2.68) |
| --- | --- | --- | --- | --- | --- | --- | --- | --- | --- |
| Total Impurities (%) |  | 0.12 | 0.25 | 13.11 | 14.27 | 0.88 | 2.17 | 11.08 | 11.77 |

|  |  | Storage Condition |  |  |  |
| --- | --- | --- | --- | --- | --- |
|  |  | 25° C. ± 2° C./ 60% RH ± 5% RH | | | |
|  |  | 1 Month | | 3 Month | |
|  | Time Point | NS | N | NS | N |
|  | Appearance | CCS | CCS | CCS | CCS |
|  | Assay (%) | 100.6 | 100.8 | 100.1 | 100.6 |
|  | pH | 4.89 | 4.9 | 4.87 | 4.87 |
|  | IMP C | 0.07 | 0.08 | 0.1 | 0.08 |
|  | IMP F | 0.11 | 0.12 | 0.16 | 0.14 |
|  | IMP G | NR | NR | NR | NR |
|  | IMP D | NR | NR | NR | NR |
|  | IMP A | NR | NR | NR | NR |
| Related Substance (%) | Unknown$_{(RRT)}$ | 0.1<br>(1.78)<br>0.09<br>(3.037) | 0.08<br>(1.78)<br>0.11<br>(3.037)<br>0.06<br>(3.578) | 0.12<br>(1.78)<br>0.14<br>(3.037) | 0.1<br>(1.78)<br>0.13<br>(3.037) |
|  | Total Impurities (%) | 0.37 | 0.46 | 0.51 | 0.45 |

BCS: Brown colored solution;
CCS—Clear colorless solution;
NR—Not Reported (<0.05%),
NT—Not Tested.
S—Aluminum overwrap with GLS 100 MBC;
NS—Aluminum overwrap with no scavenger;
N—No secondary overwrap.

TABLE 23

Table 23: Stability of Phenylephrine Hydrochloride Solution, (400 mcg/mL) in 1 mM acetate buffer with aluminum overwrap.

|  | Storage Condition | | | | | | | | | | | |
| --- | --- | --- | --- | --- | --- | --- | --- | --- | --- | --- | --- | --- |
|  |  | 60° C. | | | 40 ± 2° C./ 75 ± 5% RH | | | | 25° C. ± 2° C./ 60% RH ± 5% RH | | | |
|  |  | 2 Weeks | | | 1 Month | | 3 Month | | 1 Month | | 3 Month | |
| Time Point | Initial | S | NS | N | NS | N | NS | N | NS | N | NS | N |
| Appearance | CCS | CCS | CCS | CCS | CCS | CCS | CCS | CCS | CCS | CCS | CCS | CCS |
| Assay (%) | 100.0 | NT | NT | NT | 100.4 | 102.1 | 95.7 | 99.2 | 102.5 | 101.7 | 102.0 | 104 |
| pH | 4.94 | 4.96 | 4.98 | 4.96 | 4.93 | 4.93 | 4.93 | 4.94 | 4.96 | 4.93 | 4.93 | 4.92 |

TABLE 23-continued

Table 23: Stability of Phenylephrine Hydrochloride Solution, (400 mcg/mL) in 1 mM acetate buffer with aluminum overwrap.

| | | | Storage Condition | | | | | | | | | |
|---|---|---|---|---|---|---|---|---|---|---|---|---|
| | | | 60° C. | | | 40 ± 2° C./ 75 ± 5% RH | | | | 25° C. ± 2° C./ 60% RH ± 5% RH | | | |
| | | | | 2 Weeks | | 1 Month | | 3 Month | | 1 Month | | 3 Month | |
| Time Point | | Initial | S | NS | N | NS | N | NS | N | NS | N | NS | N |
| Related Substance (%) | Unknown$_{(RRT)}$ | NR | NT | NT | NT | NR | NR | NR | NR | NR | NR | NR | NR |
| | Total (%) | NR | NR | NR | NR | NR | NR | NR | NR | NR | NR | NR | NR |

CCS—Clear colorless solution;
NR—Not Reported (<0.05%),
NT—Not Tested.
S—Aluminum overwrap with GLS 100 MBC;
NS—Aluminum overwrap with no scavenger;
N—No secondary overwrap

TABLE 24

Table 24: Stability of Phenylephrine Hydrochloride Solution, 40 mcg/mL in 2 mM acetate buffer with aluminum overwrap.

| | | | Storage Condition | | | | | | |
|---|---|---|---|---|---|---|---|---|---|
| | | | 60° C. | | | 40 ± 2° C./ 75 ± 5% RH | | | |
| | | | 2 Weeks | | | 1 Month | | 3 Month | |
| | Time Point | Initial | S | NS | N | NS | N | NS | N |
| | Appearance | CCS | CCS | CCS | CCS | CCS | CCS | CCS | CCS |
| | Assay (%) | 100.4 | 98.8 | 100.8 | 103 | 100.3 | 100.6 | 97.7 | 97.3 |
| | pH | 4.87 | 4.88 | 4.9 | 4.87 | 4.89 | 4.88 | 4.85 | 4.84 |
| | IMP C | NR | 0.63 | 0.11 | 0.14 | 0.15 | 0.13 | 0.34 | 0.38 |
| | IMP F | NR | 1.55 | 0.33 | 0.38 | 0.18 | 0.17 | 0.52 | 0.59 |
| | IMP G | NR | 0.09 | NR | NR | NR | NR | NR | NR |
| Related Substance (%) | Unknown$_{(RRT)}$ | NR | 0.07$_{(5.67)}$ 0.3$_{(7.49)}$ 0.21$_{(9.18)}$ | 0.21$_{(9.18)}$ | NR | 0.07$_{(1.78)}$ 0.06$_{(3.58)}$ | 0.09$_{(1.78)}$ | 0.24$_{(1.78)}$ 0.14$_{(1.97)}$ 0.08$_{(2.42)}$ 0.08$_{(2.83)}$ | 0.41$_{(1.78)}$ 0.18$_{(1.97)}$ 0.12$_{(2.83)}$ |
| | Total Impurities (%) | NR | 2.86 | 0.65 | 0.51 | 0.45 | 0.40 | 1.41 | 1.68 |

| | | Storage Condition | | | |
|---|---|---|---|---|---|
| | | 25° C. ± 2° C./ 60% RH ± 5% RH | | | |
| | | 1 Month | | 3 Month | |
| | Time Point | NS | N | NS | N |
| | Appearance | CCS | CCS | CCS | CCS |
| | Assay (%) | 100.9 | 101 | 100.5 | 100.9 |
| | pH | 4.88 | 4.86 | 4.85 | 4.85 |
| | IMP C | 0.08 | 0.06 | 0.08 | 0.07 |

TABLE 24-continued

Table 24: Stability of Phenylephrine Hydrochloride Solution, 40 mcg/mL in 2 mM acetate buffer with aluminum overwrap.

|  |  |  |  |  |  |  |
|---|---|---|---|---|---|---|
|  |  | IMP F | 0.08 | 0.07 | 0.09 | 0.08 |
|  |  | IMP G | NR | NR | NR | NR |
|  | Related Substance (%) | Unknown$_{(RRT)}$ | 0.06$_{(3.578)}$ | NR | 0.08$_{(1.78)}$ | 0.11$_{(1.78)}$ |
|  |  | Total Impurities (%) | 0.21 | 0.13 | 0.24 | 0.27 |

CCS—Clear colorless solution;
NR—Not Reported (0.05%),
NT—Not Tested;
S—Aluminum overwrap with GLS 100 MBC;
NS—Aluminum overwrap with no scavenger;
N—No secondary overwrap

TABLE 25

Table 25: Stability of Phenylephrine Hydrochloride Solution, 400 mcg/mL in 2 mM acetate buffer with aluminum overwrap

|  |  | Storage Condition | | | | | | |
|---|---|---|---|---|---|---|---|---|
|  |  |  | 60° C. | | | 40 ± 2° C./ 75 ± 5% RH | | |
|  |  |  | 2 Weeks | | | 1 Month | | 3 Month |
|  | Time Point | Initial | S | NS | N | NS | N | NS | N |
|  | Appearance | CCS | CCS | BCS | BCS | BCS | BCS | BCS | BCS |
|  | Assay (%) | 99.5 | NT | NT | NT | 102.8 | 102.3 | 95.4 | 94.7 |
|  | IMP C | NR | NT | NT | NT | NR | NR | 0.2 | 0.22 |
|  | IMP F | NR | NT | NT | NT | NR | 0.08 | 0.34 | 0.34 |
|  | IMP A | NR | NT | NT | NT | NR | NR | 0.06 | 0.07 |
|  | pH | 4.89 | 4.99 | 4.75 | 4.74 | 4.95 | 4.95 | 4.77 | 4.76 |
| Related Substance (%) | Unknown$_{(RRT)}$ | NR | NT | NT | NT | 0.08$_{(1.78)}$ | 0.16$_{(1.78)}$ | 0.12$_{(0.488)}$ 0.21$_{(1.78)}$ 0.1$_{(1.965)}$ 0.3$_{(2.825)}$ 0.08$_{(2.68)}$ | 0.12$_{(0.49)}$ 0.07$_{(1.38)}$ 0.24$_{(1.78)}$ 0.09$_{(1.97)}$ 0.32$_{(2.83)}$ 0.06$_{(3.08)}$ 0.1$_{(2.68)}$ |
|  | Total Impurities (%) | NR | NT | NT | NT | 0.08 | 0.24 | 1.42 | 1.63 |

|  |  | Storage Condition | | | |
|---|---|---|---|---|---|
|  |  | 25° C. ± 2° C./ 60% RH ± 5% RH | | | |
|  |  | 1 Month | | 3 Month | |
|  | Time Point | NS | N | NS | N |
|  | Appearance | CCS | CCS | CCS | CCS |
|  | Assay (%) | 102.1 | 104.4 | 101.6 | 96.2 |
|  | IMP C | NR | NR | NR | NR |
|  | IMP F | NR | NR | NR | NR |

TABLE 25-continued

Table 25: Stability of Phenylephrine Hydrochloride Solution,
400 mcg/mL in 2 mM acetate buffer with aluminum overwrap

| | | | | | | |
|---|---|---|---|---|---|---|
| | | IMP A | NR | NR | NR | NR |
| | | pH | 4.95 | 4.96 | 4.93 | 4.9 |
| | Related Substance (%) | Unknown$_{(RRT)}$ | NR | 0.06$_{(1.38)}$ | NR | NR |
| | | Total Impurities (%) | NR | 0.06 | NR | NR |

BCS: Brown colored solution;
CCS—Clear colorless solution;
NR—Not Reported (<0.05%),
NT—Not Tested;
S—Aluminum overwrap with GLS 100 MBC;
NS—Aluminum overwrap with no scavenger;
N—No secondary overwrap Selection of metal ion chelator: Citric acid, ascorbic acid, tartaric acid and edetate disodium (EDTA) are commonly used chelating agents for parenteral drug products. Citric acid or ascorbic acid have very weak association constants compared to EDTA. Addition of these acids to the formulation would also lead to more acidic pH values. Thus, EDTA (0.01%) was screened during the initial experiments as potential metal chelator to improve stability of the solution. However, based on the results and mechanism of degradation, it was determined that there was no need of any chelating agents.

However, based on later performed stainless steel and bulk hold compatibility studies, it was observed that for lower strength (40 mcg/mL) formulations, there was a metal-initiated oxidative impurity (RRT ~2.0) observed as early as 24 hours (0.06%) of the bulk hold in the stainless steel container (316L) (see results in Table 26), which grew over time to 0.31% at 120 hrs. However, in the highest strength, 400 mcg/mL, this impurity was not observed till 96 hrs (see results in Table 27). The study was then repeated by incorporating EDTA in the formulation (10 mcg/mL), and it was observed that no impurities above the reporting threshold (>0.05%) were found at least until 48 hrs for the lowest strength, 40 mcg/mL (see results in Table 28). For the highest strength. 400 mcg/mL, no impurity above the reporting threshold (>0.05%) was observed till 96 hrs (see results in Table 29).

TABLE 26

Table 26: Results for Stainless-Steel (316L) compatibility and Bulk Hold study of
Phenylephrine Hydrochloride Solution, 40 mcg/mL without EDTA
Product Lot #13158 (pH 5.0), 40 mcg/mL

| | | | Time Point | | | | | |
|---|---|---|---|---|---|---|---|---|
| | | | Initial | | 24 HRS | | 48 HRS | | 72 HRS |
| | | Samples | C | T | C | T | C | T | C |
| | | Appearance | CCS | CCS | CCS | CCS | CCS | CCS | CCS |
| | | Assay (%) | 101.3 | 100.6 | 100.6 | 99.5 | 99.7 | 99.0 | 101.3 |
| | | pH | 4.93 | 4.98 | 5.06 | 5.02 | 5.04 | 5.02 | 5.03 |
| | | S-Form | 0.04 | NT | NT | NT | 0.05 | 0.04 | 0.05 |
| Color | L* | | 100 | 100 | 100 | 100 | 100 | 99 | 100 |
| | a* | | 0 | 0 | 0 | 0 | 0 | 0 | 0 |
| | b* | | 0 | 0 | 0 | 0 | 0.1 | 0.1 | 0.1 |
| Related Substance (%) | | Unknown$_{(RRT)}$ | NR$_{(2.25)}$ | NR$_{(2.25)}$ | NR$_{(2.25)}$ | 0.06$_{(2.0)}$ | NR | 0.11$_{(2.0)}$ | NR |
| | | Total Impurities (%) | NR | NR | NR | 0.06 | NR | 0.11 | NR |

| | | | Time Point | | | | |
|---|---|---|---|---|---|---|---|
| | | | 72 HRS | 96 HRS | | 120 HRS | |
| | | Samples | T | C | T | C | T |
| | | Appearance | CCS | CCS | CCS | CCS | CCS |
| | | Assay (%) | 101.6 | 102.5 | 102.2 | 102.5 | 102.4 |
| | | pH | 5.04 | 5.08 | 5.03 | 5.08 | 6.07 |
| | | S-Form | 0.06 | NT | NT | 0.03 | NT |
| Color | L* | | 99.9 | 99.8 | 100 | 100 | 100 |
| | a* | | 0.1 | -0.1 | 0 | 0 | 0 |

TABLE 26-continued

Table 26: Results for Stainless-Steel (316L) compatibility and Bulk Hold study of
Phenylephrine Hydrochloride Solution, 40 mcg/mL without EDTA
Product Lot #13158 (pH 5.0), 40 mcg/mL

|  |  |  |  |  |  |  |
|---|---|---|---|---|---|---|
|  | b* | 0.2 | −0.1 | 0 | 0.1 | 0.1 |
| Related | Unknown$_{(RRT)}$ | 0.16$_{(2.0)}$ | NR$_{(2.25)}$ | 0.09$_{(1.46)}$ | NR | 0.31$_{(2.0)}$ |
| Substance |  |  |  | 0.21$_{(2.0)}$ |  | 0.06$_{(1.46)}$ |
| (%) |  |  |  | NR$_{(3.60)}$ |  |  |
|  |  |  |  | 0.05$_{(4.0)}$ |  |  |
|  | Total Impurities (%) | 0.16 | NR | 0.21 | NR | 0.37 |

C—Control;
T—Test;
CCS—Clear colorless solution;
NR—Not Reported (<0.05%),
NT—Not Tested.

TABLE 27

Table 27: Results for Stainless-Steel (316L) compatibility and Bulk Hold study of
Phenylephrine Hydrochloride Solution, 400 mcg/mL without EDTA
Product Lot #13158 (pH 5.0), Phenylephrine Hydrochloride Solution, 400 mcg/mL

|  |  | Time Point | | | | | | | | | | |
|---|---|---|---|---|---|---|---|---|---|---|---|---|
|  |  | Initial | | 24 HRS | | 48 HRS | | 72 HRS | | 96 HRS | | 120 HRS | |
| Samples |  | C | T | C | T | C | T | C | T | C | T | C | T |
| Appearance |  | CCS | CCS | CCS | CCS | CCS | CCS | CCS | CCS | CCS | CCS | CCS | CCS |
| Assay (%) |  | 100 | 99.5 | 100.2 | 100.3 | 100.8 | 100.8 | 100.3 | 100.1 | 102 | 101.6 | 100.4 | 100.8 |
| pH |  | 5.08 | 5.05 | 4.93 | 4.95 | 4.96 | 4.96 | 4.97 | 5.01 | 4.96 | 4.95 | 4.98 | 4.94 |
| S-Form |  | 0.06 | 0.04 | 0.06 | NT | NT | 0.05 | 0.05 | 0.05 | 0.06 | NT | 0.07 | NT |
| Color | L* | 100.1 | 100.3 | 100.3 | 100.3 | 100.3 | 100.3 | 100.3 | 100.2 | 100 | 100 | 100 | 99.9 |
|  | a* | 0 | 0 | 0 | 0 | 0 | 0 | 0 | 0 | 0 | 0.1 | 0 | 0.1 |
|  | b* | 0 | 0 | −0.1 | −0.1 | 0.1 | −0.1 | 0 | 0 | 0 | 0 | 0 | 0.1 |
|  | Unknown$_{(RRT)}$ | NR | NR | NR | NR | NR | NR$_{(2.0)}$ NR$_{(2.25)}$ | NR | NR$_{(2.0)}$ NR$_{(3.50)}$ | NR$_{(2.25)}$ NR$_{(5.46)}$ | NR$_{(2.0)}$ NR$_{(2.25)}$ NR$_{(3.53)}$ | NR | 0.12$_{(2.0)}$ |
| Related Substance (%) | Total Impurities (%) | NR | NR | NR | NR | NR | NR | NR | NR | NR | NR | NR | 0.12 |

C—Control
T—Test;
CCS—Clear colorless solution;
NR—Not Reported (0.05%),
NT—Not Tested

TABLE 28

Table 28: Results for Stainless-Steel (316L) compatibility and Bulk Hold study of
Phenylephrine Hydrochloride Solution, 40 mcg/mL with 10 mcg/mL EDTA
Product Lot #13661 (pH 5.0), 40 mcg/mL with 10 mcg/mL EDTA

|  |  | Time Point | | | | | | | |
|---|---|---|---|---|---|---|---|---|---|
|  |  | Initial | | 24 HRS | | 48 HRS | | 72 HRS | |
| Samples |  | C | T | C | T | C | T | C | T |
| Appearance |  | CCS | CCS | CCS | CCS | CCS | CCS | CCS | CCS |
| Assay (%) |  | 100.3 | 101.1 | 100.9 | 99.9 | 100.8 | 100.4 | 100.9 | 99.8 |
| pH |  | 5.01 | 5.0 | 5.0 | 5.02 | 4.97 | 4.98 | 5.01 | 5.01 |
| Impurity F |  | NR | NR | NR | NR | NR | NR | NR | NR |
| Related Compounds (%) | Unknown$_{(RRT)}$ | NR | NR | NR | NR$_{(0.85)}$ | NR | NR 0.05$_{(0.85)}$ | NR | 0.07$_{(0.85)}$ NR$_{(1.20)}$ NR$_{(1.68)}$ |

TABLE 28-continued

Table 28: Results for Stainless-Steel (316L) compatibility and Bulk Hold study of Phenylephrine Hydrochloride Solution, 40 mcg/mL with 10 mcg/mL EDTA Product Lot #13661 (pH 5.0), 40 mcg/mL with 10 mcg/mL EDTA

| | | | | | | | | | |
|---|---|---|---|---|---|---|---|---|---|
| Total Impurities (%) | NR | NR | NR | NR | NR | NR | NR | 0.07 | |

| | | Time Point | | | |
|---|---|---|---|---|---|
| | | 96 HRS | | 168 HRS | |
| | Samples | C | T | C | T |
| | Appearance | CCS | CCS | CCS | CCS |
| | Assay (%) | 100.6 | 100.1 | 100 | 98.8 |
| | pH | 4.97 | 5.01 | 5.01 | 4.99 |
| | Impurity F | NR | 0.05 | NR | 0.13 |
| Related Compounds (%) | Unknown$_{(RRT)}$ | NR | 0.10$_{(0.62)}$ 0.13$_{0.85}$ 0.06$_{(1.68)}$ | NR | 0.32$_{(0.85)}$ 0.11$_{(1.2)}$ 0.21$_{(1.68)}$ |
| | Total Impurities (%) | NR | 0.18 | NR | 0.78 |

C—Control;
T—Test;
CCS—Clear colorless solution;—NR—Not Reported (<0.05%),
NT—Not Tested

TABLE 29

Table 29: Results for Stainless-Steel (316L) compatibility and Bulk Hold study of Phenylephrine Hydrochloride Solution, 400 mcg/mL with 10 mcg/mL EDTA Product Lot #13661 (pH 5.0), 400 mcg/mL with 10 mcg/mL EDTA

| | | Time Point | | | | | | | |
|---|---|---|---|---|---|---|---|---|---|
| | | Initial | | 24 HRS | | 48 HRS | | 72 HRS | |
| | Samples | C | T | C | T | C | T | C | T |
| | Appearance | CCS | CCS | CCS | CCS | CCS | CCS | CCS | CCS |
| | Assay (%) | 100.2 | 100.6 | 100 | 100.5 | 99.9 | 100.3 | 99.9 | 100.5 |
| | pH | 5.02 | 5.01 | 5.03 | 5.0 | 5.01 | 5.02 | 5.03 | 5.06 |
| Related Compounds (%) | Unknown$_{(RRT)}$ | NR | NR | NR | NR | NR | NR | NR | NR |
| | Total Impurities (%) | NR | NR | NR | NR | NR | NR | NR | NR |

| | | Time Point | | | |
|---|---|---|---|---|---|
| | | 96 HRS | | 168 HRS | |
| | Samples | C | T | C | T |
| | Appearance | CCS | CCS | CCS | CCS |
| | Assay (%) | 100.5 | 101.4 | 100.9 | 100.1 |
| | pH | 5.05 | 5.02 | 5.03 | 5.01 |
| Related Compounds (%) | Unknown$_{(RRT)}$ | NR | NR$_{(0.85)}$ | NR | 0.08$_{(0.85)}$ NR$_{(0.60)}$ NR$_{(1.68)}$ |
| | Total Impurities (%) | NR | NR | NR | 0.08 |

C—Control;
T—Test;
CCS—Clear colorless solution;
NR—Not Reported (0.05%),
NT—Not Tested.

An accelerated stability study (at 60° C.) was also conducted with formulations containing 10 mcg/mL EDTA in the formulation. Based on the accelerated stability results as shown in Tables 30-31, no significant change in the impurity profile was observed with formulation containing 10 mcg/mL EDTA based on the 4 weeks data.

TABLE 30

Table 30: Stability results of Phenylephrine HCl, 40 mcg/mL in 5 mM acetate buffer and 10 mcg/mL EDTA.

| | | Storage Condition | | | | | | | | | | | |
|---|---|---|---|---|---|---|---|---|---|---|---|---|---|
| | | 60° C. | | | | | | | | | | 40 ± 2° C./ 75 ± 5% RH | |
| | | Time Point | | | | | | | | | | | |
| | | Initial | | 1 Week | | 2 Week | | 3 Week | | 4 Week | | 1 M | |
| Packaging | | S | NS | S | NS | S | NS | S | NS | S | NS | S | NS |
| Appearance | | CCS | CCS | CCS | CCS | CCS | CCS | CCS | CCS | CCS | CCS | CCS | CCS |
| Assay (%) | | 100.6 | 99.5 | 100.7 | 101.6 | 102.3 | 102.4 | 100.7 | 99.6 | 101 | 102.5 | 101.8 | 102.4 |
| pH | | 5.03 | 4.96 | 5 | 4.98 | 4.93 | 4.93 | 4.96 | 4.96 | 5.02 | 4.99 | 5.04 | 4.95 |
| DO | | 1.15 | 8.71 | 1.16 | 10.45 | 2.75 | 5.77 | 1.24 | 6.34 | 1.28 | 6.12 | 0.89 | 6.05 |
| Impurity F | | NR | NR | NR | 0.05 | 0.05 | 0.07 | 0.07 | 0.06 | 0.07 | 0.08 | NR | NR |
| Related Substance | Unknown$_{(RRT)}$ | NR$_{(1.20)}$ | NR$_{(1.20)}$ | NR$_{(1.20)}$ | NR$_{(1.20)}$ | NR$_{(1.20)}$ | NR$_{(1.20)}$ | NR$_{(1.20)}$ NR$_{(1.90)}$ | NR$_{(1.20)}$ | NR$_{(1.20)}$ | NR$_{(1.20)}$ | NR$_{(1.20)}$ | NR$_{(1.20)}$ |
| (%) | Total Impurities (%) | NR | NR | NR | 0.05 | 0.05 | 0.07 | 0.07 | 0.06 | 0.06 | 0.08 | NR | NR |

S—Aluminum overwrap with Scavenger,
NS—Clear overwrap with no scavenger;
CCS—Clear colorless solution;
NR—Not Reported (<0.05%),
NT—Not Tested

TABLE 31

Table 31: Stability results of Phenylephrine HCl, 400 mcg/mL in 5 mM acetate buffer and 10 mcg/mL EDTA

| | | Storage Condition | | | | | | | | | | | |
|---|---|---|---|---|---|---|---|---|---|---|---|---|---|
| | | 60° C. | | | | | | | | | | 40 ± 2° C./ 75 ± 5% RH | |
| | | Time Point | | | | | | | | | | | |
| | | Initial | | 1 Week | | 2 Week | | 3 Week | | 4 Week | | 1 M | |
| Packaging | | S | NS | S | NS | S | NS | S | NS | S | NS | S | NS |
| Appearance | | CCS | CCS | CCS | CCS | CCS | CCS | CCS | CCS | CCS | CCS | CCS | CCS |
| Assay (%) | | 98.9 | 98.3 | 101.2 | 101.2 | 100.9 | 101.6 | 99.9 | 100.5 | 99.8 | 100.7 | 0.79 | 6.26 |
| pH | | 4.97 | 4.95 | 5.03 | 5.02 | 5 | 4.99 | 4.98 | 5.02 | 5.06 | 5.06 | 5.02 | 5.02 |
| DO | | 1.34 | 10.65 | 1.19 | 8.73 | 1.21 | 5.94 | 1.73 | 6.05 | 1.39 | NT | 99.9 | 101.4 |
| Impurity F | | NR | NR | NR | NR | NR | NR | NR | NR | NR | NR | NR | NR |
| Related Substance | Unknown$_{(RRT)}$ | NR | NR | NR | NR | NR | NR | NR | NR | NR$_{(1.20)}$ | NR$_{(1.20)}$ | NR | NR |
| (%) | Total Impurities (%) | NR | NR | NR | NR | NR | NR | NR | NR | NR | NR | NR | NR |

S—Aluminum overwrap with Scavenger,
NS—Clear overwrap with no scavenger;
CCS—Clear colorless solution;
NR—Not Reported (<0.05%),
NT—Not Tested As used herein, the term "administering" a pharmaceutical composition or drug refers to both direct and indirect administration of the pharmaceutical composition or drug, wherein direct administration of the pharmaceutical composition or drug is typically performed by a health care professional (e.g., physician, nurse, etc.), and wherein indirect administration includes a step of providing or making available the pharmaceutical composition or drug to the health care professional for direct administration (e.g., via injection, infusion, oral delivery, topical delivery, etc.). It should further be noted that the terms "prognosing" or "predicting" a condition, a susceptibility for development of a disease, or a response to an intended treatment is meant to cover the act of predicting or the prediction (but not treatment or diagnosis of) the condition, susceptibility and/or response, including the rate of progression, improvement, and/or duration of the condition in a subject.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the full scope of the present disclosure, and does not pose a limitation on the scope of the invention otherwise claimed. No language in the specification should be construed as indicating any non-claimed element essential to the practice of the claimed invention.

It should be apparent to those skilled in the art that many more modifications besides those already described are possible without departing from the full scope of the concepts disclosed herein. The disclosed subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A ready-to-administer sterile antioxidant free phenylephrine composition, comprising:
    phenylephrine or salt thereof at a concentration of equal or less than 0.4 mg/ml;
    a buffer comprising acetic acid, wherein the acetic acid is present in an amount of about 0.3 mg/mL; and
    a metal ion chelator, wherein the metal ion chelator is present in an amount of equal or less than 10 mcg/mL;
    wherein no more than 0.5% degradation products are formed from degradation of the phenylephrine upon storage of the phenylephrine composition over a period of at least six months at 25° C., and
    wherein the composition has a pH of between 4.0 and 5.5.

2. The composition of claim 1, wherein the phenylephrine or salt thereof is present in the composition at a concentration of about 0.04 mg/ml.

3. The composition of claim 1, wherein the phenylephrine or salt thereof is present in the composition at a concentration of about 0.08 mg/ml.

4. The composition of claim 1, wherein the phenylephrine or salt thereof is present in the composition at a concentration of about 0.16 mg/ml.

5. The composition of claim 1, wherein the phenylephrine or salt thereof is present in the composition at a concentration of about 0.4 mg/ml.

6. The composition of claim 1, wherein the composition has a pH of about 5.0.

7. The composition of claim 1, wherein the composition is packaged in a flexible polymer bag, wherein the flexible polymer bag is further packaged in a metallized pouch that optionally contains an oxygen scavenger.

8. The composition of claim 1, further comprising a tonicity agent selected from the group consisting of sodium chloride, glycerol, thioglycerol, mannitol, lactose, and dextrose.

9. The composition of claim 1, wherein the metal ion chelator is ethylene diamine tetra acetic acid (EDTA).

10. A method of manufacturing a ready-to-administer sterile antioxidant free phenylephrine composition, comprising: formulating a buffered liquid including phenylephrine or salt thereof; wherein the buffered composition comprises an acetate buffer and has a pH of between 4.5 and 5.5, and optionally further comprises a metal ion chelator; wherein the phenylephrine or salt thereof is present in the buffered liquid at a concentration of equal or less than 0.4 mg/ml; and terminally sterilizing the liquid composition; wherein no more than 0.25% degradation products are formed from degradation of the phenylephrine upon storage of the phenylephrine composition over a period of at least six months at 25° C.

11. The method of claim 10, wherein the buffered liquid comprises water for injection.

12. The method of claim 10, wherein the acetate buffer has a concentration of equal or less than 5 mM.

13. The method of claim 10, wherein the composition has a pH of about 5.0.

14. The method of claim 10, further comprising a step of packaging the composition into a flexible polymer bag and packaging the flexible polymer bag into a metallized pouch that optionally contains an oxygen scavenger.

15. The method of claim 10, wherein the composition comprises the metal ion chelator, wherein the metal ion chelator is ethylene diamine tetra acetic acid (EDTA), and wherein the metal ion chelator is present in an amount of equal or less than 10 mcg/mL.

16. The method of claim 10, wherein the composition further comprises a tonicity agent selected from the group consisting of sodium chloride, glycerol, thioglycerol, mannitol, lactose, and dextrose.

17. The method of claim 10 wherein terminally sterilizing the liquid composition comprises autoclaving the liquid composition.

18. A ready-to-administer sterile antioxidant free phenylephrine composition, essentially consisting of:
    phenylephrine or salt thereof at a concentration of between about 0.04 mg/ml and about 0.4 mg/ml;
    a buffer comprising acetic acid, wherein the acetic acid is present in an amount of about 0.3 mg/mL; and
    a metal ion chelator, wherein the metal ion chelator is present in an amount of equal or less than 10 µg/mL;

wherein no more than 0.5% degradation products are formed from degradation of the phenylephrine upon storage of the phenylephrine composition over a period of at least six months at 25° C., and wherein the composition has a pH of between 4.0 and 5.5.

19. The composition of claim 18, wherein phenylephrine or salt thereof is present at a concentration of about 0.04 mg/ml, or at a concentration of about 0.08 mg/ml, or at a concentration of about 0.16 mg/ml, or at a concentration of about 0.4 mg/ml.

* * * * *